US012696862B2

(12) United States Patent
Swinkels

(10) Patent No.: US 12,696,862 B2
(45) Date of Patent: Aug. 4, 2026

(54) CUCUMBER VARIETY NUN 13088 CUL

(71) Applicant: Nunhems B.V., Nunhem (NL)

(72) Inventor: Robert Swinkels, Nunhem (NL)

(73) Assignee: Nunhems B.V., Nunhem (NL)

( * ) Notice: Subject to any disclaimer, the term of this patent is extended or adjusted under 35 U.S.C. 154(b) by 281 days.

(21) Appl. No.: 18/514,118

(22) Filed: Nov. 20, 2023

(65) Prior Publication Data

US 2024/0081213 A1 Mar. 14, 2024

(30) Foreign Application Priority Data

Nov. 23, 2022 (CA) ..................................... 3183340

(51) Int. Cl.
| | |
|---|---|
| *A01H 5/08* | (2018.01) |
| *A01H 1/00* | (2006.01) |
| *A01H 6/34* | (2018.01) |

(52) U.S. Cl.
CPC ............... *A01H 6/346* (2018.05); *A01H 1/00* (2013.01); *A01H 5/08* (2013.01)

(58) Field of Classification Search
None
See application file for complete search history.

(56) References Cited

U.S. PATENT DOCUMENTS

| | | | |
|---|---|---|---|
| 4,822,949 | A | 4/1989 | Niego et al. |
| 5,349,128 | A | 9/1994 | Quemada et al. |
| 5,492,827 | A | 2/1996 | Dirks |
| 6,084,152 | A | 7/2000 | Kwak et al. |
| 2015/0126380 | A1 | 5/2015 | Van Dun |
| 2015/0245570 | A1 | 9/2015 | Vogelaar et al. |
| 2017/0335339 | A1 | 11/2017 | Van Dun et al. |
| 2018/0054990 | A1 | 3/2018 | Haaring et al. |
| 2021/0137044 | A1* | 5/2021 | Swinkels ................. A01H 5/08 |

OTHER PUBLICATIONS

"Applying for a Plant Variety Certificate of Protection", USDA, https://www.ams.usda.gov/services/pv po/application-help/apply, downloaded May 1, 2023.*
UPOV, Explanatory Notes on Essentially Derived Varieties Under the 1991 Act of the UPOV Convention, Apr. 6, 2017.*
Ex Parte C, USPQ 2d 1492 (1992).*
Ex Parte McGowen Board Decision in U.S. Appl. No. 14/996,093, decided Jun. 15, 2020.*
Y: Haun et al., Plant Physiology, Feb. 2011, vol. 155, pp. 645-655.*
Z: Großkinsky et al., J. Exp. Bot., vol. 66, No. 11, pp. 5429-5440, 2015.*
AA: Plant & Soil Sciences eLibrary 2023, downloaded Aug. 26, 2023.*
"Calibration Book-Cucumber", Naktuinbouw Calibration Book, Cucumis Sativus—Cucumber & Gherkin, Version 1, Dec. 2010, 70 pages.

"Cucumber", Western Institute for Food safety and security(WIFSS), http://www.wifss.ucdavis.edu/wpcontent/uploads/2016/05/FDA_WIFSS_-Cucumbers_PDF.pdf, May 2016, pp. 1-6.
"Cucumber, Gherkin, UPOV Code: CUCUM_SAT, (*Cucumis sativus* L.)", Guidelines for the conduct of tests for distinctness, uniformity and stability, UPOV, International Union for the Protection of New Varieties of Plants, Geneva, TG/61/7, Mar. 13, 2019, 48 pages.
"High wire cultivation", Nunhems, 2022, https://www.nunhems.com/gb/en/solutions/high-wire.html.
"Objective description of Cucumber (*Cucumis sativus* L.)", US Department of Agriculture, Agricultural Marketing Service, Science and Technology, Plant Variety Protection Office, Exhibit C, Jun. 2015, 3 pages.
Colijn-Hooymans, et al., "Competence for regeneration of cucumber cotyledons is restricted to specific developmental stages", Plant Cell, Tissue and Organ Culture, vol. 39, Dec. 1994, pp. 211-217.
Kim, et al., "Callus growth and plant regeneration in diverse cultivars of cucumber (*Cucumis sativus* L.)", Plant Cell, Tissue and Organ Culture, vol. 12, Issue 1, Mar. 1988, pp. 67-74.
Needleman, et al., "A general method applicable to the search for similarities in the amino acid sequence of two proteins", Journal of Molecular Biology, vol. 48, Issue 3, 1970, pp. 443-453.
Nikolova, et al., "Diploidization of cucumber (*Cucumis sativus* L.) haploids by colchicine treatment", Acta Societas Botanicorum Poloniae, vol. 65, Issue 3-4, 1996, pp. 311-317.
Parvathaneni, et al., "Fingerprinting in Cucumber and Melon (*Cucumis* spp.) Genotypes Using Morphological and ISSR Markers", Journal of Crop Science and Biotechnology, vol. 14, Issue 1, Mar. 2011, pp. 39-43.
Rice, et al., "Emboss: The European Molecular Biology Open Software Suite", Trends in Genetics, vol. 16, Issue 6, Jun. 1, 2000, pp. 276-277.
Robert W. Allard, "Principles of Plant Breeding", Second edition, 1999, pp. 64-67.
Sarreb, et al., "Comparison of triploid and diploid cucumber in long-term liquid cultures", Plant Cell, Tissue and Organ Culture, vol. 71, Dec. 2002, pp. 231-235.
Schrader, et al., "Cucumber Production in California", University of California Agriculture and Natural Resources, Publication 8050, 2002, pp. 1-8.
Songstad, et al., "Genome Editing of Plants", Critical Reviews in Plant Sciences, vol. 36, Issue 1, 2017, pp. 1-23.
Vidavsky, et al., "Tomato Breeding Lines Resistant and Tolerant to Tomato Yellow Leaf Curl Virus Issued from *Lycopersicon hirsutum*", Phytopathology, vol. 88, Issue 9, Sep. 1998, pp. 910-914.
Vos, et al., "AFLP: a new technique for DNA fingerprinting", Nucleic Acids Research, vol. 23, Issue 21, Nov. 11, 1995, pp. 4407-4414.
Wijnker, et al., "Hybrid recreation by reverse breeding in *Arabidopsis thaliana*", Nature Protocols, vol. 9, Issue 4, Mar. 6, 2014, pp. 761-772.

* cited by examiner

*Primary Examiner* — Phuong T Bui
(74) *Attorney, Agent, or Firm* — ArentFox Schiff LLP

(57) ABSTRACT

A plant of variety NUN 13088 CUL is disclosed as well as seeds and plants and fruits thereof. NUN 13088 CUL is a Dutch long cucumber variety comprising high resistance to *Podosphaera xanthii* and Cucumber Green Mottle Mosaic Virus (CGMMV).

21 Claims, 6 Drawing Sheets

CUCUMBER VARIETY NUN 13088 CUL

CROSS-REFERENCE TO RELATED APPLICATION

This application claims priority of Canadian Patent Application No. 3183340 filed on Nov. 23, 2022, which is hereby incorporated by reference in its entirety.

FIELD OF THE DISCLOSURE

The disclosure relates to the field of plant breeding, specifically to cucumber variety NUN 13088 CUL. The disclosure further relates to vegetative reproductions of cucumber variety NUN 13088 CUL, methods for tissue culture of cucumber variety NUN 13088 CUL and regenerating a plant from such a tissue culture and to phenotypic variants of cucumber variety NUN 13088 CUL. The disclosure also relates to progeny of cucumber variety NUN 13088 CUL and the hybrid varieties obtained by crossing cucumber variety NUN 13088 CUL as a parent line with plants of other varieties or parent lines.

BACKGROUND OF THE DISCLOSURE

The goal of plant breeding is to combine various desirable traits in a single variety. Such desirable traits may include greater yield, resistance to diseases, insects or other pests, tolerance to heat and drought, better agronomic quality, higher nutritional value, enhanced growth rate, and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype. Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential.

Cucumber (*Cucumis sativus* L.) belongs to the Cucurbitaceae family and is naturally a diploid (2n=14) outcrossing species, although haploid, doubled-haploid (see, e.g., U.S. Pat. No. 5,492,827, which is hereby incorporated by reference in its entirety), and triploid (see, e.g., Sarreb et al. (2002), Plant Cell Tissue, Organ Culture 71: 231-235) types have been developed. The fruit of cucumber is typically cylindrical and elongated. It has thin, dark green skin and mild flavor, which can be eaten without peeling.

In the United States, the fourth largest cucumber producer, the slicing (fresh market) and pickling (processing) are the two main types of cucumber fruit grown commercially. Varieties and production methods are typically adapted to the end use. Slicing cucumbers are often longer, larger and have darker and thicker skin, whereas pickling/processing cucumbers have shorter fruit, thinner skin with interior flesh that make them more amenable to pickling. Seedless varieties are generally preferable for both fresh and processing markets as seeds are not palatable.

Cucumber plants that set fruit parthenocarpically (without pollination and fertilization) have more recently been available. These plants produce seedless fruit unless pollinated. Growth of parthenocarpic varieties is beneficial in that setting of fruit on these cultivars does not produce an inhibiting effect on plant growth, unlike the case of fertilized, seeded fruit. The seedless varieties are usually higher yielding and of higher quality due to the lack of seeds. However, growth of these plants requires isolation from seeded cucumbers to avoid pollination and subsequent seeded fruit.

Most of the cucumbers currently grown for processing (for pickles and pickle products) in the United States are seeded hybrid varieties. Hybrid varieties offer the advantages of easy combination of dominant and recessive traits, such as disease resistance, from a set of inbred parents, as well as careful control of parentage. The production of F1 hybrid cucumber seeds from a pollen parent bearing only male flowers has been reported (see, e.g., U.S. Pat. No. 4,822,949).

Advances in biotechnology have also resulted in genetically engineered cucumber plants with improved traits. For example, cucumbers resistant to Cucumber Mosaic Virus (CMV) have been developed by expression of CMV protein coat genes (see, e.g., U.S. Pat. No. 5,349,128). Transgenic plants exhibiting, for example, other viral resistance traits or high levels of superoxide dismutase have also been reported (see, e.g., U.S. Pat. No. 6,084,152).

While breeding efforts to date have provided a number of useful cucumber varieties with beneficial traits, there remains a great need in the art for new varieties with further improved traits. Such plants would benefit farmers and consumers alike by improving crop yields and/or quality. Breeding objectives include varying the color, texture, and flavor of the fruit, minimizing the occurrence of bitterness, optimizing flesh thickness, solid content (% dry matter), storage properties, and sugar content. Breeding programs also focus on developing plants with earlier fruit maturity, more restricted vine growth, improved disease resistance or tolerance, and improved adaptability to environmental conditions.

SUMMARY OF THE VARIOUS ASPECTS OF THE DISCLOSURE

The disclosure provides for cucumber variety NUN 13088 CUL, products thereof, and methods of using the same. NUN 13088 CUL is a Dutch long cucumber variety of the Kasja type and is suitable for growing in a greenhouse. The fruit of cucumber variety NUN 13088 CUL has dark green color with deep ribbed dark fruit and good neck. The fruits are uniforms and well filled.

Cucumber variety NUN 13088 CUL is a flexible variety that has a good generative nature with plenty of vegetative body. It is high yielding and has well-balanced plant type with strong and large leaf and good fruit quality. This single fruited variety is early to mature and therefore, early to harvest. It also has fast lateral transition making it ideal for short crop production.

Cucumber variety NUN 13088 CUL performs ideally in the spring, summer, and early fall plantings. The planting window ranges from February until September in the traditional environment. Due to the flexibility of this variety, it can also be planted in spring high wire conditions. Due to the strength of this variety, it is possible to allow for a few extra fruit on the main stem to help increase yield. It can easily fit into medium size production and does not abort easily.

In another aspect, the plant of variety NUN 13088 CUL, or part thereof, or progeny thereof comprises high resistance to *Podosphaera xanthii* and Cucumber Green Mottle Mosaic Virus (CGMMV), measured according to TG/61/7.

In another aspect, the plant of variety NUN 13088 CUL has 14, 15, or more, or all of the following distinguishing characteristics when compared to the Reference Variety as shown in Table 4, when determined at 5% significance level for numerical characteristics and determined by type or degree for non-numerical characteristics for plants grown under the same environmental conditions.

1. longer 3rd internode length;
2. longer stem length (total length of first 15 internodes);
3. predominantly one flower per node;
4. very early female flower development;
5. longer mature leaf length;
6. larger mature leaf width;
7. longer mature leaf petiole length;
8. larger mature petiole diameter;
9. dark green mature leaf color (RHS N137A);
10. absence of yellowish blossom end stripes;
11. dark green predominant color at stem end (RHS N137A);
12. mature fruit ends blunt or rounded;
13. darker intensity of ground color of skin;
14. very weak to weak creasing; and
15. sparse vestiture.

In another aspect, the disclosure provides a plant or a progeny having all the physiological and morphological characteristics of variety NUN 13088 CUL when grown under the same environmental conditions. In another aspect, the plant or progeny has all or all but one, two, or three of the physiological and morphological characteristics of cucumber variety NUN 13088 CUL when measured under the same environmental conditions and e.g., evaluated at significance levels of 1%, 5%, or 10% significance (which can also be expressed as a p-value) for quantitative characteristics and identical (same type or degree) for non-quantitative characteristics, wherein a representative sample of seed of variety NUN 13088 CUL has been deposited under Accession Number NCIMB 44043. In another aspect, the plant or progeny has all or all but one, two, or three of the physiological and morphological characteristics as listed in Tables 1-3 for variety NUN 13088 CUL when measured under the same environmental conditions and e.g., evaluated at significance levels of 1%, 5% or 10% significance (which can also be expressed as a p-value) for quantitative characteristics and identical (same type or degree) for non-quantitative characteristics.

In another aspect, the disclosure provides a seed of cucumber variety NUN 13088 CUL, wherein a representative sample of said seed has been deposited under Accession Number NCIMB 44043. The disclosure also provides for a plurality of seeds of cucumber variety NUN 13088 CUL.

The cucumber seed of variety NUN 13088 CUL may be provided as an essentially homogeneous population of cucumber seed. The population of seed of cucumber variety NUN 13088 CUL may be particularly defined as essentially free from other seed. The seed population may be grown into plants to provide an essentially homogeneous population of cucumber plants as described herein.

The disclosure also provides a plant grown from a seed of cucumber variety NUN 13088 CUL and a plant part thereof.

In another aspect, the disclosure provides for a hybrid variety of NUN 13088 CUL.

The disclosure also provides for a progeny of variety NUN 13088 CUL. In another aspect, the disclosure provides a plant or a progeny retaining all or all but one, two, or three of the "distinguishing characteristics" or all or all but one, two, or three of the "morphological and physiological characteristics" of variety NUN 13088 CUL and methods for producing that plant or progeny.

In another aspect, the disclosure provides a seed growing or grown on a plant of variety NUN 13088 CUL (i.e., produced after pollination of the flower of cucumber variety NUN 13088 CUL). The disclosure also provides an F1 progeny of cucumber variety NUN 13088 CUL.

The disclosure furthermore provides a cucumber fruit produced on a plant grown from a seed of cucumber variety NUN 13088 CUL.

In another aspect, the disclosure provides for a plant part obtained from variety NUN 13088 CUL, wherein said plant part is: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, a cotyledon, a scion, a stock, a rootstock, a pistil, an anther, or a flower or a part thereof. Fruits are particularly important plant parts. In another aspect, the plant part obtained from variety NUN 13088 CUL is a cell, optionally a cell in a cell or tissue culture. That cell may be grown into a plant of variety NUN 13088 CUL.

The disclosure also provides a cell culture of cucumber variety NUN 13088 CUL and a plant regenerated from cucumber variety NUN 13088 CUL, wherein the plant has all the characteristics of cucumber variety NUN 13088 CUL, when grown under the same environmental conditions, as well as methods for culturing and regenerating cucumber variety NUN 13088 CUL. Alternatively, a regenerated plant may have one characteristic that is different from cucumber variety NUN 13088 CUL.

The disclosure further provides a vegetatively propagated plant of variety NUN 13088 CUL having all or all but one, two, or three of the morphological and physiological characteristics of cucumber variety NUN 13088 CUL when grown under the same environmental conditions.

In another aspect, the disclosure provides a method of producing a cucumber plant comprising crossing cucumber variety NUN 13088 CUL with itself or with another cucumber variety and selecting a progeny cucumber plant from said crossing.

The disclosure also provides a method of producing a cucumber plant derived from cucumber variety NUN 13088 CUL.

In a further aspect, the disclosure provides a method of producing a hybrid cucumber seed comprising crossing a first parent cucumber plant with a second parent cucumber plant and harvesting the resultant hybrid cucumber seed, wherein said first parent plant or second parent cucumber plant is cucumber variety NUN 13088 CUL. Also provided is a hybrid cucumber seed produced from crossing a first parent cucumber plant and second parent cucumber plant and harvesting the resultant hybrid cucumber seed, wherein said first parent cucumber plant or second parent cucumber plant is cucumber variety NUN 13088 CUL. Moreover, the hybrid cucumber plant grown from the hybrid cucumber seed is provided.

In another aspect, the disclosure provides a method of introducing a single locus conversion into the plant of variety NUN 13088 CUL, wherein a representative sample of seed of said cucumber variety has been deposited under Accession Number NCIMB 44043, wherein the plant otherwise retains all of the physiological and morphological characteristics of cucumber variety NUN 13088 CUL and further comprises the single locus conversion.

In yet another aspect, the disclosure provides a method of introducing a desired trait into cucumber variety NUN 13088 CUL, said method comprises transforming the plant of cucumber variety NUN 13088 CUL with a transgene that confers the desired trait, wherein the transformed plant otherwise has all of the physiological and morphological characteristics of cucumber variety NUN 13088 CUL and contains the desired trait.

The disclosure also provides a method of producing a modified cucumber plant with a desired trait, wherein the method comprises mutating a cucumber plant or plant part of cucumber variety NUN 13088 CUL, wherein a representative sample of seed of said cucumber variety has been deposited under Accession Number NCIMB 44043, and wherein the mutated plant otherwise retains all of the physiological and morphological characteristics of cucumber variety NUN 13088 CUL and contains the desired trait.

In one aspect, the single locus conversion or desired trait is yield, size, compactness, dry matter content, firmness, flavor, fruit quality, enhanced nutritional quality, post-harvest quality, storage properties, color, male sterility, herbicide tolerance, insect resistance, pest resistance, disease resistance, Powdery mildew resistance without necrosis, environmental stress tolerance, modified carbohydrate metabolism, modified protein metabolism, or ripening.

In another aspect, the disclosure provides a container comprising the plant, plant part, or seed of cucumber variety NUN 13088 CUL.

Also provided is a food, a feed, or a processed product comprising the plant part of cucumber variety NUN 13088 CUL, wherein the plant part is a fruit or part thereof.

DEFINITIONS

Figure 1:
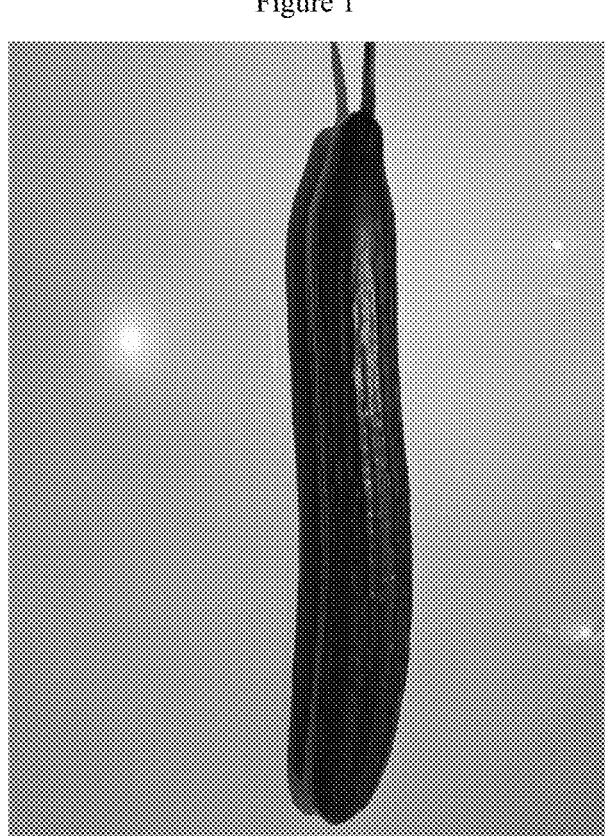
FIG. 1 shows the fruit of cucumber variety NUN 13088 CUL based on 2022 trials.
Figure 2:
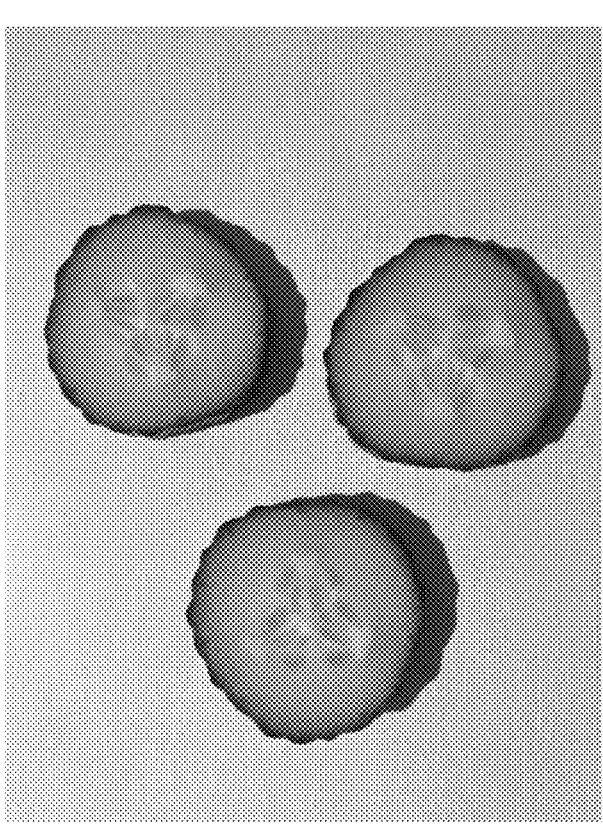
FIG. 2 shows the cross-section of cucumber variety NUN 13088 CUL based on 2022 trials.
Figure 3:
FIG. 3 shows the fruit of cucumber variety NUN 13088 CUL based on 2023 trials.
Figure 4:
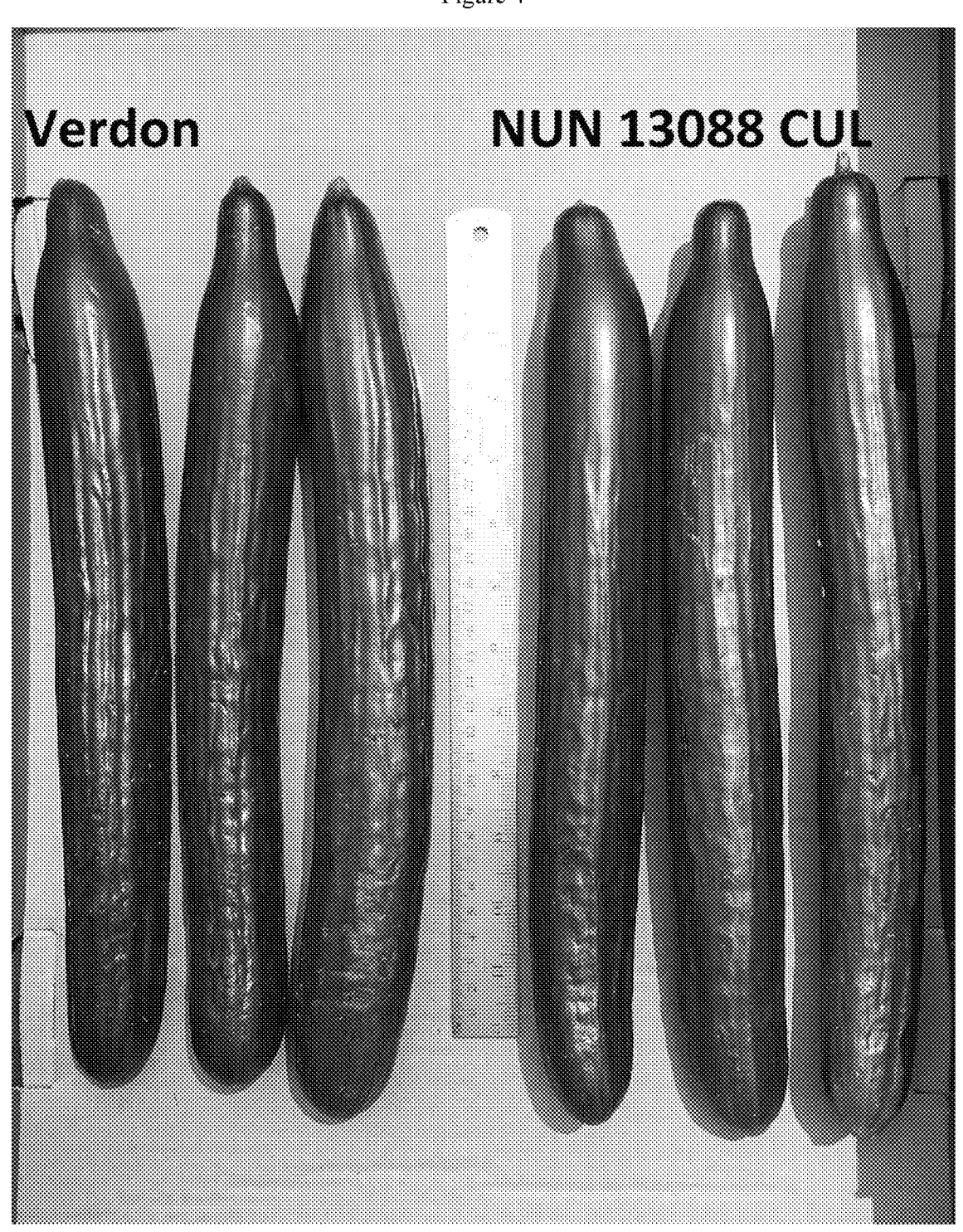
FIG. 4 shows the fruit comparison of cucumber variety NUN 13088 CUL and the Reference Variety based on 2023 trials.
Figure 5:
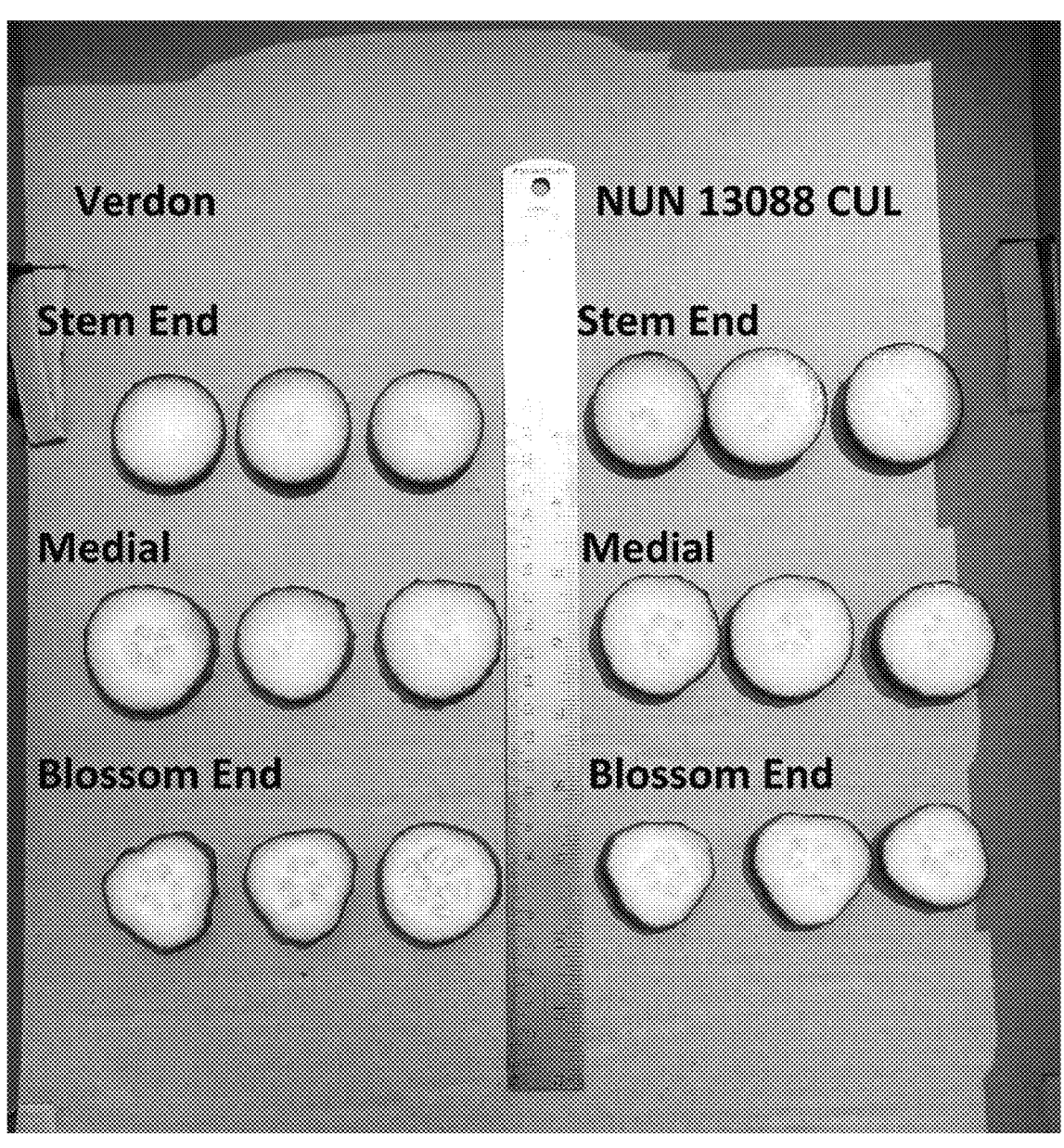
FIG. 5 shows the cross section of cucumber variety NUN 13088 CUL and the Reference Variety based on 2023 trials.
Figure 6:
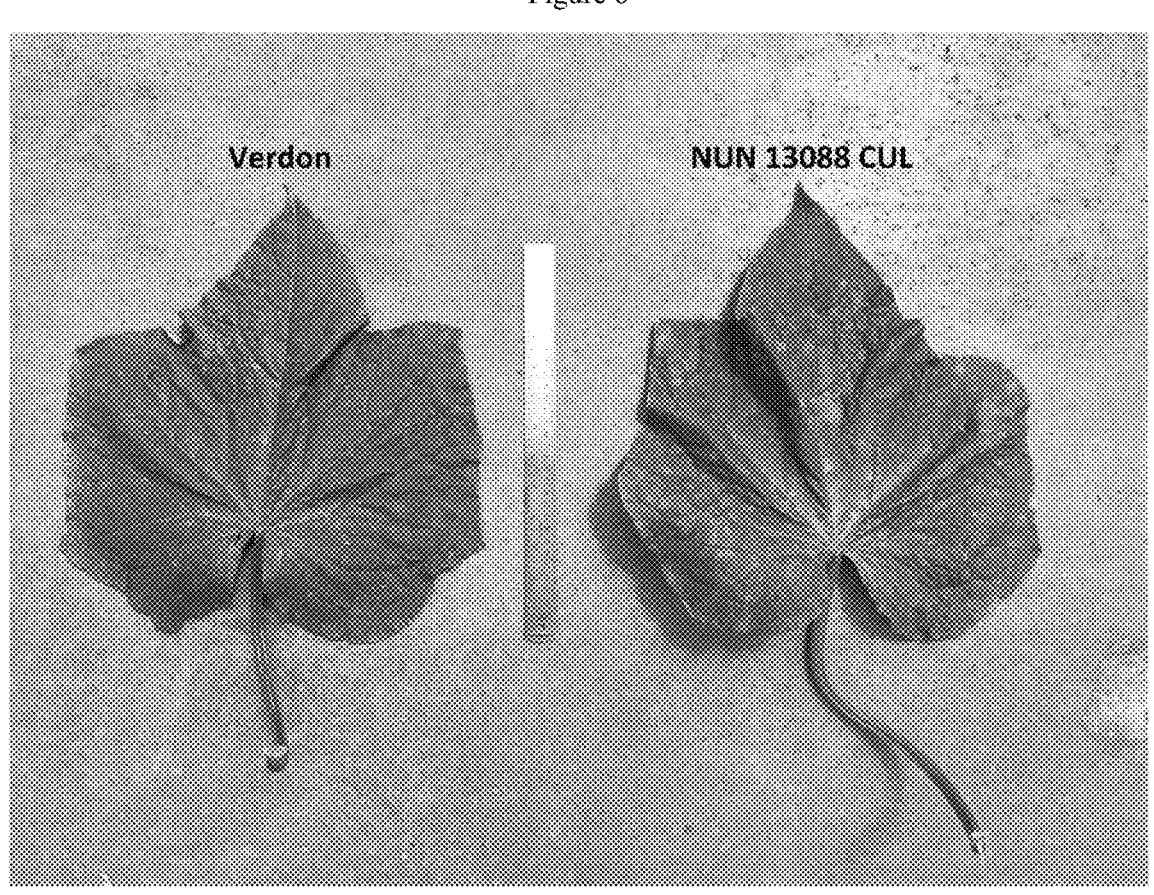
FIG. 6 shows the leaf comparison of cucumber variety NUN 13088 CUL and the Reference Variety based on 2023 trials.

"Cucumber" refers herein to plants of the species *Cucumis sativus*. The most commonly eaten part of a cucumber is the fruit or pepo. The fruit comprises a stem and peduncle or pedicel, receptacle, ectocarp, rind, fruit flesh, exocarp, mesocarp, external phloem, internal phloem, xylem, vascular bundle, carpel, placenta and optionally seed. The stem and peduncle or pedicel, receptacle, ectocarp, rind, fruit flesh, exocarp, mesocarp, external phloem, internal phloem, xylem, vascular bundle, carpel, placenta and seed coat of the seed are maternal tissues and are genetically identical to the plant on which they grow.

"Cultivated cucumber" refers to plants of *Cucumis sativus* i.e., varieties, breeding lines or cultivars of the species *C. sativus*, cultivated by humans and having good agronomic characteristics.

The terms "cucumber plant designated NUN 13088 CUL," "NUN 13088 CUL," "NUN 13088," "NUN 13088 F1," "13088 CUL," "cucumber 13088," or "Dunavin" are used interchangeably herein and refer to a cucumber plant of variety NUN 13088 CUL, representative seed of which having been deposited under Accession Number NCIMB 44043.

A "seed of NUN 13088 CUL" refers to a cucumber seed which can be grown into a plant of variety NUN 13088 CUL, wherein a representative sample of viable seed of variety NUN 13088 CUL has been deposited under Accession Number NCIMB 44043. A seed can be in any stage of maturity, for example, a mature, viable seed, or an immature, non-viable seed. A seed comprises an embryo and maternal tissues.

An "embryo of NUN 13088 CUL" refers to an "F1 hybrid embryo" as present in a seed of cucumber variety NUN 13088 CUL, a representative sample of said seed of NUN 13088 CUL having been deposited under Accession Number NCIMB 44043.

A "seed grown on NUN 13088 CUL" refers to a seed grown on a mature plant of variety NUN 13088 CUL or inside a fruit of cucumber variety NUN 13088 CUL. The "seed grown on NUN 13088 CUL" contains tissues and DNA of the maternal parent, cucumber variety NUN 13088 CUL. When said seed is planted, it grows into a first generation progeny plant of variety NUN 13088 CUL.

A "fruit of NUN 13088 CUL" refers to a fruit containing maternal tissues of cucumber variety NUN 13088 CUL as deposited under Accession Number NCIMB 44043. In one aspect, the fruit contains seed grown on cucumber variety NUN 13088 CUL. In another aspect, the fruit does not contain seed, i.e., the fruit is parthenocarpic. The skilled person is familiar with methods for inducing parthenocarpy. Those methods comprise chemically or genetically inducing parthenocarpy. Compounds suitable for chemically inducing parthenocarpy include auxins, gibberellins and cytokinins. Genetic parthenocarpy can be induced (see, e.g., US 2018/0054990 and US 2017/0335339 (PIN4)) or can be provided by reduced or eliminated expression of PISTILATA (PI) or APETALA3 (AP3). A fruit can be in any stage of maturity, for example, a mature fruit in the yellow stage comprising viable seed, or an immature fruit in the edible green stage comprising non-viable seed.

"Plant" includes the whole plant or any part or derivatives thereof having the same genetic makeup as the plant from which it is obtained.

"Plant part" includes any part of a plant, such as a plant organ (e.g., harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, a hypocotyl, a cotyledon, a scion, a graft, a stock, a rootstock, a pistil, an anther, and a flower or part thereof. Seed can be mature or immature. Pollen or ovules may be viable or non-viable. Also, any developmental stage is included, such as seedlings, cuttings prior or after rooting, mature plants or leaves. Alternatively, a plant part may also include a plant seed which comprise s maternal tissues of cucumber variety NUN 13088 CUL and an embryo having one or two sets of chromosomes derived from the parent plant, e.g., from cucumber variety NUN 13088 CUL. Such an embryo comprises two sets of chromosomes derived from cucumber variety NUN 13088 CUL if it is produced from self-pollination of cucumber variety NUN 13088 CUL, while an embryo derived from cross-fertilization of cucumber variety NUN 13088 CUL, will comprise only one set of chromosomes from cucumber variety NUN 13088 CUL, and the other set of chromosomes from the other parent.

An "essentially homogeneous population of cucumber seed" is a population of seeds where at least 97%, 98%, 99% or more of the total population of seeds are seeds of cucumber variety NUN 13088 CUL.

An "essentially homogeneous population of cucumber plants" is a population of plants where at least 97%, 98%, 99% or more of the total population of plants are plants of variety NUN 13088 CUL.

The phrase "essentially free from other seed" refers to a population of seed where less than 3%, 2%, 1% or less of the total population of seed is seed that is not a cucumber seed or, in another aspect, less than 3%, 2%, 1% or less of the total population of seed is seed that is not a seed of cucumber variety NUN 13088 CUL.

"Harvest maturity" refers to the stage at which a cucumber fruit is ripe or ready for harvest or the optimal time to harvest the fruit for the market, for processing or for consumption. In one aspect, harvest maturity is the stage which allows proper completion of the normal ripening.

"Flavor" refers to the sensory impression of a food or other substance, especially a cucumber fruit or fruit part (fruit flesh) and is determined mainly by the chemical senses of taste and smell. Flavor is influenced by texture properties and by volatile and/or non-volatile chemical components (organic acids, lipids, carbohydrates, salts etc.).

"Aroma" refers to smell (or odor) characteristics of cucumber fruits or fruit parts (fruit flesh).

"Yield" means the total weight of all cucumber fruits harvested per hectare of a particular line or variety. It is understood that "yield" expressed as weight of all cucumber fruits harvested per hectare can be obtained by multiplying the number of plants per hectare times the "yield per plant".

"Marketable yield" means the total weight of all marketable cucumber fruits, especially fruit which is not cracked, damaged or diseased, harvested per hectare of a particular line or variety. A "marketable fruit" is a fruit that has commercial value.

"Harvested plant material" refers herein to plant parts (e.g., fruits detached from the whole plant), which have been collected for further storage and/or further use.

"USDA descriptors" are the plant variety descriptors described for cucumber in the "Objective Description of Variety—Cucumber (*Cucumis sativus* L.)," as published by the US Department of Agriculture, Agricultural Marketing Service, Plant Variety Protection Office, Beltsville, MD 20705. "Non-USDA descriptors" are other descriptors suitable for describing cucumber.

"UPOV descriptors" are the plant variety descriptors described for cucumber in the "Guidelines for the Conduct of Tests for Distinctness, Uniformity and Stability, TG/61/7 (Geneva 2007, revised 2019 Mar. 13), as published by UPOV (International Union for the Protection of New Varieties and Plants) and which can be downloaded from the world-wide web at upov.int/edocs/tgdocs/en/tg061.pdf. Likewise, "UPOV methods" to determine specific parameters for the characterization of cucumber are described at upov.int.

"Calibration Book for Cucumber & Gherkin" refers to the calibration book for cucumbers and gherkins which provides guidance for describing a cucumber variety, as published by Naktuinbouw (version 1, December 2010). The calibration book is based on the CPVO (Community Plant Variety Protection Office) Protocol CPVO-TP/06/12 and UPOV Guideline TG/6/1/7.

"RHS" or "RHS color chart" refers to the color chart of the Royal Horticultural Society (UK), which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart 2007.

"Reference Variety for Cucumber Variety NUN 13088 CUL" refers herein to variety Verdon, a commercial variety from Rijk Zwaan, which has been planted in a trial together with cucumber variety NUN 13088 CUL. In Tables 2 and 3, the characteristics of cucumber variety NUN 13088 CUL are compared with the characteristics of the Reference Variety. The distinguishing characteristics between cucumber variety NUN 13088 CUL and the Reference Variety are described in Table 4.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g., the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Tables 1-3 or "all or all but one, two or three of the physiological and morphological characteristics" of Tables 1-3.

The physiological and/or morphological characteristics mentioned above are commonly evaluated at significance levels of 1%, 5% or 10% if they are numerical, or for having an identical degree (or type) if not numerical, measured under the same environmental conditions. For example, a progeny plant or a Single Locus Converted plant or a mutated plant of variety NUN 13088 CUL, may have one or more (or all) of the essential physiological and/or morphological characteristics of said variety listed in Tables 1-3, as determined at the 5% significance level (i.e., $p<0.05$), when grown under the same environmental conditions.

"Distinguishing characteristics" or "distinguishing morphological and/or physiological characteristics" refers herein to the characteristics which distinguish the new variety from other cucumber varieties, such as the Reference Variety (i.e., are different), when grown under the same environmental conditions. The distinguishing characteristics between cucumber variety NUN 13088 CUL and the Reference Variety are described herein in Table 4. When comparing cucumber variety NUN 13088 CUL to other varieties, the distinguishing characteristics may be different. In one aspect, the distinguishing characteristics may include one, two, three, or more (or all) of the characteristics listed in Tables 1-3. Preferably, all numerical distinguishing characteristics are statistically significantly different at p<0.05 between cucumber variety NUN 13088 CUL or the other variety (e.g., the Reference Variety).

Cucumber variety NUN 13088 CUL has the following distinguishing characteristics when compared to the Reference Variety as shown in Table 4, when determined at 5% significance level for numerical characteristics and determined by type or degree for non-numerical characteristics for plants grown under the same environmental conditions.

1. longer 3rd internode length;
2. longer stem length (total length of first 15 internodes);
3. predominantly one flower per node;
4. very early female flower development;
5. longer mature leaf length;
6. larger mature leaf width;
7. longer mature leaf petiole length;
8. larger mature petiole diameter;
9. dark green mature leaf color (RHS N137A);
10. absence of yellowish blossom end stripes;
11. dark green predominant color at stem end (RHS N137A);
12. mature fruit ends blunt or rounded;
13. darker intensity of ground color of skin;
14. very weak to weak creasing; and
15. sparse vestiture.

Thus, a cucumber plant "comprising the distinguishing characteristics of cucumber variety NUN 13088 CUL" (such as a progeny plant) refers herein to a plant which does not differ significantly from said variety in the distinguishing characteristics above, when determined at 5% significance level for numerical characteristics and determined by type or degree for non-numerical characteristics for plants grown under the same environmental conditions. Therefore, in one aspect, a cucumber plant is provided which does not differ significantly from cucumber variety NUN 13088 CUL.

Similarity and differences between two different plant lines or varieties can be determined by comparing the number of morphological and/or physiological characteristics that are the same (i.e., statistically not significantly different) or that are different (i.e., statistically significantly different) between the two plant lines or varieties using plants grown under the same environmental conditions. Preferably, a numerical characteristic is considered to be "the same" when the value for a numeric characteristic is not significantly different at the 1% (p<0.01) or 5% (p<0.05) significance level, using a T-test, a standard method known to the skilled person. Preferably, non-numerical or "degree" or "type" characteristics are considered "the same" when the values have the same "degree" or "type" when scored using USDA and/or UPOV descriptors if the plants are grown under the same environmental conditions.

In one aspect, a statistical analysis of the quantitative characteristics showing the degree of significance may be provided. Statistical significance is the likelihood that a relationship between two or more variables is caused by something other than chance, i.e., that the differences in the means for quantitative characteristics of the plant of cucumber variety NUN 13088 CUL and the Reference Variety are significant due to chance. For the purpose of proving differences or distinction between cucumber variety NUN 13088 CUL and the Reference Variety, a p-value of 5% or 0.05 or lower is considered statistically significant. This means that there is only a 5% probability or lower probability that the observed result could have happened just by chance or random variation.

The statistical analysis is drawn from a small sample of at least 15 plants or plant parts of cucumber variety NUN 13088 CUL and the Reference Variety. Statistical points or parameters such as mean, minimum, median, maximum, and standard deviation are collected from the sample data to analyze where the average is, how varied the data set is, and whether the data is skewed. For the purpose of determining whether the result of the data set is statistically significant, a T-Test is used, a statistical tool for proving significance in the means of the two groups (e.g., cucumber variety NUN 13088 CUL and the Reference Variety) at 5% significance level (a p-value of 5% or 0.05).

"Variety" or "cultivar" means a plant grouping within a single botanical taxon of the lowest rank.

A "plant line" is, for example, a breeding line which can be used to develop one or more varieties. A breeding line is typically highly homozygous.

"Harvested seeds" refer to seeds harvested from a line or variety, e.g., produced after self-fertilization or cross-fertilization and collected.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Locus" (plural loci) refers to the specific location, place or site of a DNA Sequence on a chromosome where, for example, a gene or genetic marker is found. A locus may confer a specific trait.

"Allele" refers to one or more alternative forms of a gene locus. All of these loci relate to one trait. Sometimes, different alleles can result in different observable phenotypic traits, such as different pigmentation. However, many variations at the genetic level result in little or no observable variation. If a multicellular organism has two sets of chromosomes, i.e., diploid, these chromosomes are referred to as homologous chromosomes. Diploid organisms have one copy each of gene (and therefore one allele) on each chromosome. If both alleles are the same, they are homozygotes. If the alleles are different, they are heterozygotes.

"Genotype" refers to the genetic composition of a cell or organism.

"Phenotype" refers to the detectable characteristics of a plant, a cell, or an organism, which characteristics are the manifestation of gene expression.

"Haploid" refers to a cell or organism having one set of two sets of chromosomes in a diploid.

"Diploid" refers to a plant, a vegetative plant part(s), or seed having two sets of chromosomes, designated herein as 2n.

"Triploid" refers to a plant, a vegetative plant part (s), or seed having three sets of chromosomes, designated herein as 3n.

"Tetraploid" refers to a plant, vegetative plant part(s), or seed having four sets of chromosomes, designated herein as 4n.

"Rootstock" or "stock" refers to the plant selected for its roots, in particular for the resistance of the roots to diseases or stress (e.g., heat, cold, salinity etc.). Normally, the quality of the fruit of the plant providing the rootstock is less important.

"Scion" refers to a part of the plant attached to the rootstock. This plant is selected for its stems, leaves, flowers, or fruits. The scion contains the desired genes to be duplicated in future production by the stock/scion plant and may produce the desired cucumber fruit.

"Stock/scion" or "grafted plant" refers to a cucumber plant comprising a rootstock from one plant grafted to a scion from another plant.

"Grafting" refers to the method of joining of (genetically) different plant parts, especially scions and rootstocks, together so that they grow as a single plant. A grafted seedlings or a grafted plant is a seedling or plant (produced by grafting) consisting of such different plant parts and which grows as one plant.

"Tissue culture" or "cell culture" refers to a composition comprising isolated cells of the same or a different type or a collection of such cells organized into parts of a plant. Tissue culture of various tissues of cucumber and regeneration of plants therefrom is well known and widely published (see, e.g., Sang-Gu et al. (1988), Plant Cell, Tissue and Organ Culture 12: 67-74; Colijn-Hooymans (1994), Plant Cell, Tissue and Organ Culture 39: 211-217). Similarly, methods of preparing cell cultures are known in the art.

"Vegetative propagation," "vegetative reproduction," or "clonal propagation" are used interchangeably herein and mean a method of taking a plant part and inducing or allowing that plant part to form at least roots, and also refer to the plant or plantlet obtained by that method. Optionally, the vegetative propagation is grown into a mature plant. The skilled person is aware of what plant parts are suitable for use in the method.

"Regeneration" refers to the development of a plant from cell culture, or tissue culture, or vegetative propagation.

The term "traditional breeding techniques" encompasses herein crossing, selfing, selection, doubled haploid production, embryo rescue, protoplast fusion, marker assisted selection, mutation breeding etc. as known to the breeder (i.e., methods other than genetic modification/transformation/transgenic methods), by which, for example, a genetically heritable trait can be transferred from one cucumber line or variety to another.

"Crossing" refers to the mating of two parent plants. The term encompasses "cross-pollination" and "selfing".

"Selfing" refers to self-pollination of a plant, i.e., the transfer of pollen from the anther to the stigma of the same plant.

"Cross-pollination" refers to the fertilization by the union of two gametes from different plants.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 13088 CUL. A progeny may be obtained by regeneration of cell culture or tissue culture or parts of a plant of said variety or selfing of a plant of said variety or by producing seeds of a plant of said variety. In further aspects, progeny may also encompass plants obtained from crossing of at least one plant of said variety with another cucumber plant of the same variety or another variety or line, or with wild cucumber plants. A progeny may comprise a mutation or a transgene. A "first generation progeny" is the progeny directly derived from, obtained from, obtainable from or derivable from the parent plant by, e.g., traditional breeding methods (selfing and/or cross-pollinating) or regeneration (optionally combined with transformation or mutation). Thus, a plant of variety NUN 13088 CUL is the male parent, the female parent or both of a first generation progeny of cucumber variety NUN 13088 CUL. Progeny may have all the physiological and morphological characteristics of cucumber variety NUN 13088 CUL, when grown under the same environmental conditions. Using methods such as backcrossing, recurrent selection, mutation, or transformation, one or more specific characteristics may be introduced into said variety, to provide or a plant comprising all but 1, 2, or 3 of the morphological and physiological characteristics of cucumber variety NUN 13088 CUL.

The terms "gene converted" or "conversion plant" or "single locus converted plant" in this context refer to cucumber plants which are developed by traditional breeding techniques, e.g., backcrossing or via genetic engineering or through mutation breeding, wherein essentially all of the desired morphological and physiological characteristics of the parent variety or line are recovered, in addition to the one or more characteristics introduced into the parent via e.g., the backcrossing technique (optionally including reverse breeding or reverse synthesis of breeding lines). It is understood that not only the addition of a further characteristic (e.g., addition of gene conferring a further characteristic, such as a disease resistance gene), but also the replacement/modification of an existing characteristic by a different characteristic is encompassed herein (e.g., mutant allele of a gene can modify the phenotype of a characteristic).

Likewise, a "Single Locus Converted (Conversion) Plant" refers to plants developed by plant breeding techniques comprising or consisting of mutation and/or by genetic transformation and/or by traditional breeding techniques, such as backcrossing, wherein essentially all of the desired morphological and physiological characteristics of a cucumber variety are recovered in addition to the characteristics of the single locus having been transferred into the variety via the abovementioned technique, or wherein the morphological and physiological characteristics of the variety has been replaced/modified in the variety. In case of a hybrid, the gene may be introduced or modified in the male or female parental line.

"Transgene" or "chimeric gene" refers to a genetic locus comprising a DNA Sequence which has been introduced into the genome of the plant by transformation. A plant comprising a transgene stably integrated into its genome is referred to as "transgenic plant."

As used herein, the terms "resistance" and "tolerance" are used interchangeably to describe plants that show no symptoms or significantly reduced symptoms to a specified biotic pest, pathogen, abiotic influence, or environmental condition compared to a susceptible plant. These terms are optionally also used to describe plants showing some symptoms but that are still able to produce marketable product with an acceptable yield.

"Average" refers herein to the arithmetic mean.

The term "mean" refers to the arithmetic mean of several measurements. The mean, if not indicated otherwise within this application, refers to the arithmetic mean of measurements on at least 15 different, randomly selected plants of a variety or line.

DETAILED DESCRIPTION OF THE VARIOUS
ASPECTS OF THE DISCLOSURE

The disclosure relates to a plant of variety NUN 13088 CUL, wherein a representative sample of seeds of said variety has been deposited under the Budapest Treaty, with Accession Number NCIMB 44043. NUN 13088 CUL is a Dutch long cucumber variety and is suitable for growing in a greenhouse. The fruit of cucumber variety NUN 13088 CUL has dark green color with deep ribbed dark fruit and good neck. The fruits are uniforms and well filled.

Cucumber variety NUN 13088 CUL is a flexible variety that has a good generative nature with plenty of vegetative body. It is high yielding and has well-balanced plant type with strong and large leaf and good fruit quality. This single fruited variety is early to mature and therefore, early to harvest. It also has fast lateral transition making it ideal for short crop production.

Cucumber variety NUN 13088 CUL performs ideally in the spring, summer, and early fall plantings. The planting window ranges from February until September in the traditional environment. Due to the flexibility of this variety, it can also be planted in spring high wire conditions. Due to the strength of this variety, it is possible to allow for a few extra fruit on the main stem to help increase yield. It can easily fit into medium size production and does not abort easily.

In another aspect, the plant of variety NUN 13088 CUL, or part thereof, or progeny thereof comprises high resistance to *Podosphaera xanthii*, and Cucumber Green Mottle Mosaic Virus (CGMMV), measured according to TG/61/7.

The disclosure also provides a cucumber plant or part thereof having all of the physiological and morphological characteristics of the plant of cucumber variety NUN 13088 CUL when grown under the same environmental conditions.

In another aspect, the plant of cucumber variety NUN 13088 CUL, or part thereof, of progeny plant thereof, comprises all of the morphological and physiological characteristics (i.e., average values, as indicated on the USDA Objective description of variety—cucumber, unless indicated otherwise) as shown in Tables 1-3, when determined at the 5% significance level for numerical characteristics and determined by type or degree for non-numerical characteristics for plants grown under the same environmental conditions. A part of this plant is also provided.

The disclosure further provides a cucumber plant which does not differ from the physiological and morphological characteristics of the plant of cucumber variety NUN 13088 CUL as determined at the 1%, 2%, 3%, 4% or 5% significance level for numerical characteristics and identical (same type or degree) for non-numerical characteristics when grown under the same environmental conditions. In a particular aspect, the plants are measured in the same trial (e.g., the trial is conducted as recommended by the USDA or UPOV). The disclosure also comprises a part of said plant, preferably a fruit or a part thereof.

The disclosure further relates to a cucumber variety NUN 13088 CUL, which when compared to the Reference Variety has the following distinguishing characteristics as shown in Table 4, when determined at the 5% significance level for numerical characteristics and determined by type or degree for non-numerical characteristics for plants grown under the same environmental conditions.

1. longer 3rd internode length;
2. longer stem length (total length of first 15 internodes);
3. predominantly one flower per node;
4. very early female flower development;
5. longer mature leaf length;
6. larger mature leaf width;
7. longer mature leaf petiole length;
8. larger mature petiole diameter;
9. dark green mature leaf color (RHS N137A);
10. absence of yellowish blossom end stripes;
11. dark green predominant color at stem end (RHS N137A);
12. mature fruit ends blunt or rounded;
13. darker intensity of ground color of skin;
14. very weak to weak creasing; and
15. sparse vestiture.

The morphological and/or physiological differences between two different individual plants described herein (e.g., between cucumber variety NUN 13088 CUL and a progeny of said variety) or between a plant of variety NUN 13088 CUL or progeny of said variety, or a plant having all, or all but 1, 2, or 3, of the physiological and morphological characteristics of cucumber variety NUN 13088 CUL (or all, or all but 1, 2, or 3 of the characteristics as listed in Tables 1-3) and another known variety can easily be established by growing said variety next to each other or next to the other variety (in the same field, under the same environmental conditions), preferably in several locations which are suitable for said cucumber cultivation, and measuring morphological and/or physiological characteristics of a number of plants (e.g., to calculate an average value and to determine the variation range/uniformity within the variety). Various characteristics, for example, days from seeding to market maturity, plant habit, plant growth and sex, stem form, fruit skin color, fruit neck shape, fruit tapering, skin thickness, toughness, and luster, flavor, disease resistance, insect resistance, can be measured and directly compared for species of cucumber.

Thus, the disclosure comprises a cucumber plant having one, two, or three physiological or morphological characteristics which are different from those of the plant of variety NUN 13088 CUL and which otherwise has all the physiological and morphological characteristics of the plant of variety NUN 13088 CUL, when determined (e.g., at the 5% significance level for quantitative characteristics and identical for non-numerical characteristics) for plants grown under the same environmental conditions. In another aspect, the different characteristic is affected by a mutation, optionally induced mutation, or by transformation.

The disclosure also relates to a seed of cucumber variety NUN 13088 CUL wherein a representative sample of said seed has been deposited under the Budapest Treaty, with Accession Number NCIMB 44043.

In another aspect, a seed of hybrid variety NUN 13088 CUL is obtainable by crossing the male parent of cucumber variety NUN 13088 CUL with the female parent of cucumber variety NUN 13088 CUL and harvesting the seeds produced on the female parent. The resultant seeds of said variety can be grown to produce plants of cucumber variety NUN 13088 CUL.

The disclosure also provides a plant grown from a seed of cucumber variety NUN 13088 CUL and plant part thereof, wherein a representative sample of seed has been deposited under Accession Number NCIMB 44043.

The disclosure also provides a cucumber fruit produced on a plant grown from a seed of cucumber variety NUN 13088 CUL, wherein a representative sample of seed has been deposited under Accession Number NCIMB 44043.

In another aspect, the disclosure provides for a cucumber plant part of variety NUN 13088 CUL, preferably a fruit or part thereof, a representative sample of seed from said variety has been deposited under the Budapest Treaty, with Accession Number NCIMB 44043.

Also provided is a plant of variety NUN 13088 CUL, or a fruit, or other plant part thereof, produced from a seed, wherein a representative sample of said seeds has been deposited under the Budapest Treaty, with Accession Number NCIMB 44043.

Also provided is a plant part obtained from variety NUN 13088 CUL, wherein said plant part is a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said variety, a hypocotyl, a cotyledon, a scion, a stock, a rootstock, a pistil, an anther, and a flower or a part thereof. Such plant parts may be suitable for sexual reproduction (e.g., a pollen, a flower, an ovary, an ovule, an embryo, etc.), vegetative reproduction (e.g., a cutting, a root, a stem, a cell, a protoplast, a leaf, a cotyledon, a meristem, etc.) or tissue culture (e.g., a leaf, a pollen, an embryo, a cotyledon, a hypocotyl, a cell, a root, a root tip, an anther, a flower, a seed, a stem, etc.). Fruits are particularly important plant parts. Fruits may be parthenocarpic, or seedless, or contain immature or nonviable seeds, or contain viable seeds.

In a further aspect, the plant part obtained from variety NUN 13088 CUL is a cell, optionally a cell in a cell or tissue culture. That cell may be grown into a plant of variety NUN 13088 CUL. A part of the plant of variety NUN 13088 CUL (or of a progeny of that variety or of a plant having all physiological and/or morphological characteristics but one, two, or three which are different from those of cucumber variety NUN 13088 CUL, further encompasses any cells, tissues, organs obtainable from the seedlings or plants in any stage of maturity.

The disclosure also provides a tissue or cell culture comprising cells of cucumber variety NUN 13088 CUL. Such a tissue culture can, for example, be grown on plates or in liquid culture, or be frozen for long term storage. The cells of cucumber variety NUN 13088 CUL used to start the culture can be selected from any plant part suitable for vegetative reproduction, or in a particular aspect can be cells of an embryo, a meristem, a cotyledon, a hypocotyl, pollen, a leaf, an anther, a root, a root tip, a pistil, a petiole, a flower, a fruit, a seed or a stem. In another particular aspect, the tissue culture does not contain somaclonal variation or has reduced somaclonal variation. The skilled person is familiar with methods to reduce or prevent somaclonal variation, including regular re-initiation.

In one aspect, the disclosure provides a cucumber plant regenerated from the tissue or cell culture of cucumber variety NUN 13088 CUL, wherein the regenerated plant is not significantly different from cucumber variety NUN 13088 CUL, in all, or all but one, two, or three, of the physiological and morphological characteristics, e.g., determined at the 5% significance level for numerical characteristics and identical (same type or degree) for non-numerical characteristics, when grown under the same environmental conditions. Optionally, the plant has one, two, or three the physiological or morphological characteristics that are affected by a mutation or by transformation with a transgene.

In another aspect, the disclosure provides a cucumber plant regenerated from the tissue or cell culture of cucumber variety NUN 13088 CUL, wherein the plant has all or all but one, two, or three of the physiological and morphological characteristics of said variety, e.g., determined at the 5% significance level for numerical characteristics and identical (same type or degree) for non-numerical characteristics, when grown under the same environmental conditions. Similarity or difference of a characteristic is determined by measuring that characteristics on a representative number of plants grown under the same environmental conditions, determining whether the type/degree characteristics are the same and determining whether numerical characteristics are different at the 5% significance level.

Cucumber variety NUN 13088 CUL, or its progeny, or a plant having all physiological and/or morphological characteristics but one, two, or three which are different from those of cucumber variety NUN 13088 CUL, can also be reproduced using vegetative reproduction methods. Therefore, the disclosure provides for a method of producing a plant, or a plant part, of cucumber variety NUN 13088 CUL, comprising vegetative propagation of said variety. Vegetative propagation comprises regenerating a whole plant from a plant part of variety NUN 13088 CUL or from a progeny or from or a plant having all physiological and/or morphological characteristics of said variety but one, two, or three different characteristics, such as a cutting, a cell culture, or a tissue culture.

The disclosure also provides methods of vegetatively propagating a part of the plant of variety NUN 13088 CUL. In certain aspects, the method comprises: (a) cultivating tissue or cells capable of being propagated from cucumber variety NUN 13088 CUL to obtain proliferated shoots; and (b) rooting said proliferated shoots, to obtain rooted plantlets. Steps (a) and (b) may also be reversed, i.e., first cultivating said tissue to obtain roots and then cultivating the tissue to obtain shoots, thereby obtaining rooted plantlets. The rooted plantlets may then be further grown, to obtain plants. In one aspect, the method further comprises step (c) growing plants from said rooted plantlets. Therefore, the method also comprises regenerating a whole plant from a part of the plant of variety NUN 13088 CUL. In a particular aspect, the part of the plant to be propagated is is a cutting, a cell culture, or a tissue culture.

The disclosure also provides for a vegetatively propagated plant of variety NUN 13088 CUL, or part thereof (or from progeny of said variety or from or a plant having all but one, two, or three physiological and/or morphological characteristics of cucumber variety NUN 13088 CUL), wherein the plant or part thereof has all of the morphological and physiological characteristics of cucumber variety NUN 13088 CUL, e.g., determined at the 5% significance level for numerical characteristics and identical (same type or degree) for non-numerical characteristics, when grown under the same environmental conditions. In another aspect, the propagated plant has all but one, two, or three of the morphological and physiological characteristics of cucumber variety NUN 13088 CUL, e.g., determined at the 5% significance level for numerical characteristics and identical (same type or degree) for non-numerical characteristics, when grown under the same environmental conditions.

In another aspect, the plant and plant parts of cucumber variety NUN 13088 CUL and progeny of said variety are provided, e.g., grown from seeds, produced by sexual or vegetative reproduction, regenerated from the above-described plant parts, or regenerated from a cell or tissue culture of cucumber variety NUN 13088 CUL, in which the reproduced (seed propagated or vegetatively propagated) plant has all of the physiological and morphological characteristics of cucumber variety NUN 13088 CUL. In one aspect, said progeny of cucumber variety NUN 13088 CUL can be modified in one, two, or three characteristics, in which the modification is a result of mutagenesis or transformation with a transgene.

In another aspect, the disclosure provides a method for producing a cucumber plant part, preferably a fruit, comprising growing the plant of variety NUN 13088 CUL until it sets at least one fruit, and collecting the fruit. Preferably, the fruit is collected at harvest maturity. In another aspect, the fruit is collected when the seed is ripe.

In another aspect, the plant of variety NUN 13088 CUL can be produced by seeding directly in the soil (e.g., the field) or by germinating the seeds in a controlled environment (e.g., a greenhouse) and optionally then transplanting the seedlings into the field. For example, a seed is sown into a prepared seed bed in a field where the plant remains for its entire life. Alternatively, the cucumber seed may be planted through a black plastic mulch. The dark plastic will absorb heat from the sun, warming the soil early. It will also help to conserve moisture during the growing season, controls weed and makes harvesting easier and cleaner. Tunnel row covers are also used for protection against frost and wind, optionally with drip of irrigation system (see, e.g., Schrader, et. al., University of California Agriculture and Natural Resources, Publication 8050, 2002, 1-8). Cucumber can also be grown on poles or trellises to keep the fruit suspended or entirely in the greenhouse (available at world-wide web at wifss.ucdavis.edu under wp-content/uploads/2016/05/FDA-_WIFSS_-Cucumbers_PDF.pdf). High wire cultivation system and the use of artificial lightning have also been introduced for year-round production of cucumber (available at world-wide web at nunhems.com under gb/en/solutions/high-wire.html).

In still another aspect, the disclosure provides a method of producing a cucumber plant, comprising crossing the plant of variety NUN 13088 CUL with a second cucumber plant at least once, allowing seed to develop and optionally harvesting said progeny seed. The skilled person can select progeny from said crossing. Optionally, the progeny (grown from the progeny seed) is crossed twice, thrice, or four, five, six or seven times, and allowed to set seed. In one aspect, the first "crossing" further comprises planting seeds of a first and a second parent cucumber plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

The disclosure also provides a method for collecting pollen of cucumber variety NUN 13088 CUL, comprising collecting pollen from the plant of variety NUN 13088 CUL. Alternatively, the method comprises growing a plant of variety NUN 13088 CUL until at least one flower contains pollen and collecting the pollen. In a particular aspect, the pollen is collected when it is mature or ripe. A suitable method for collecting pollen comprises collecting anthers or the part of the anther that contains pollen, for example, by cutting the anther or the part of the anther off. Pollen can be collected in a container. Optionally, collected pollen can be used to pollinate a cucumber flower.

In still another aspect, the disclosure provides a method of producing a cucumber plant, comprising selfing the plant of variety NUN 13088 CUL one or more times, and selecting a progeny cucumber plant from said selfing. In one aspect, the progeny plant retains all or all but one, two, or three of the physiological and morphological characteristic of cucumber variety NUN 13088 CUL, when grown under the same environmental conditions. In a different aspect, the progeny plant comprises all of the physiological and morphological characteristic of cucumber variety NUN 13088 CUL of Tables 1-3.

The disclosure also provides a method for developing a cucumber plant in a breeding program, using the plant of cucumber variety NUN 13088 CUL, or its parts as a source of plant breeding material. Suitable plant breeding techniques are recurrent selection, backcrossing, pedigree breeding, mass selection, mutation breeding and/or genetic marker enhanced selection. In one aspect, the method comprises crossing cucumber variety NUN 13088 CUL or its progeny, or a plant comprising all but 1, 2, or 3 or more of the morphological and physiological characteristics of cucumber variety NUN 13088 CUL (e.g., as listed in Tables 1-3), with a different cucumber plant, and wherein one or more offspring of the crossing are subject to one or more plant breeding techniques: recurrent selection, backcrossing, pedigree breeding, mass selection, mutation breeding and genetic marker enhanced selection (see, e.g., Vidaysky and Czosnek, (1998) Phytopathology 88(9): 910-4).

In other aspects, the disclosure provides a progeny plant of variety NUN 13088 CUL, such as a progeny plant obtained by further breeding of cucumber variety NUN 13088 CUL. Further breeding with cucumber variety NUN 13088 CUL includes selfing that variety and/or cross-pollinating said variety with another cucumber plant one or more times. In a particular aspect, the disclosure provides for a progeny plant that retains all the morphological and physiological characteristics of cucumber variety NUN 13088 CUL, or in another aspect, a progeny plant that retains all, or all but one, two, or three of the morphological and physiological characteristics of cucumber variety NUN 13088 CUL, optionally all or all but one, two, or three of the characteristics as listed in Tables 1-3, determined at the 5% significance level for numerical characteristics and identical for non-numerical characteristics, when grown under the same environmental conditions. In another aspect, the progeny is a first generation progeny, i.e., the ovule or the pollen (or both) used in the crossing is an ovule or pollen of cucumber variety NUN 13088 CUL, where the pollen comes from an anther of cucumber variety NUN 13088 CUL, and the ovule comes from an ovary of cucumber variety NUN 13088 CUL. In another aspect, the disclosure provides for a vegetative reproduction of the variety and a plant having all, or all but 1, 2, or 3 of the physiological and morphological characteristics of cucumber variety NUN 13088 CUL (e.g. as listed in Tables 1-3).

In one aspect, pedigree selection is used as a breeding method for developing a cucumber variety. Pedigree selection is also known as the "Vilmorin System of Selection," see, e.g., Allard, John Wiley & Sons, Inc., 1999, 64-67. In general, selection is first practiced among F2 plants. In the next season, the most desirable F3 lines are first identified, then desirable F3 plants within each line are selected. The following season and in all subsequent generations of inbreeding, the most desirable families are identified first, then desirable lines within the selected families are chosen. A family refers to lines that were derived from plants selected from the same progeny from the preceding generation.

Thus, progeny in connection with pedigree selection are either the generation (seeds) produced from the first cross (F1) or selfing (51), or any further generation produced by crossing and/or selfing (F2, F3, etc.) and/or backcrossing (BC1, BC2, etc.) one or more selected plants of the F1 and/or 51 and/or BC1 generation (or plants of any further generation, e.g., F2) with another cucumber plant (and/or with a wild relative of cucumber). Progeny may have all the physiological and morphological characteristics of cucumber variety NUN 13088 CUL, when grown under the same environmental conditions and/or progeny may have (be selected for having) one or more of the distinguishing characteristics of cucumber variety NUN 13088 CUL.

In yet a further aspect, the disclosure provides for a method of producing a new cucumber plant. The method comprises crossing cucumber variety NUN 13088 CUL, or a plant comprising all but 1, 2, or 3 of the morphological and physiological characteristics of cucumber variety NUN 13088 CUL, (as listed in Tables 1-3), or a progeny thereof, either as male or as female parent, with a second cucumber plant (or a wild relative of cucumber) one or more times, and/or selfing a cucumber plant of variety NUN 13088 CUL or a progeny plant thereof, one or more times, and selecting progeny from said crossing and/or selfing. The second cucumber plant may, for example, be a line or variety of the species *C. sativus* L., *Cucumis hystrix, Cucumis ritchiei* (syn. *Dicaelospermum ritchiei*) or *Cucumis maderaspatana* (syn. *Mukia maderaspatana*).

In a further aspect, cucumber variety NUN 13088 CUL is used in crosses with other different cucumber varieties to produce first generation (F1) cucumber hybrid seeds and plants with superior characteristics. In a particular aspect, the disclosure provides a cucumber seed and a cucumber plant produced by crossing a first parent cucumber plant with a second parent cucumber plant, wherein at least one of the first or second parent cucumber plant is cucumber variety NUN 13088 CUL. In another aspect, the cucumber seed and cucumber plant produced are the first filial generation (F1) cucumber seed and plant produced by crossing the plant of cucumber variety NUN 13088 CUL with another cucumber plant.

The morphological and physiological characteristics of cucumber variety NUN 13088 CUL are provided in Tables 1-3, as collected in a trial according to USDA and/or UPOV standards. Encompassed herein is also a plant obtainable from cucumber variety NUN 13088 CUL (e.g., by selfing and/or crossing and/or backcrossing with said variety and/or progeny of said variety) comprising all or all but one, two, or three of the physiological and morphological characteristics of cucumber variety NUN 13088 CUL as listed in Tables 1-3 (e.g., as determined at the 5% significance level for numerical characteristics and identical for non-numerical characteristics), when grown under the same environmental conditions and/or comprising one or more (or all; or all except one, two, or three) characteristics when grown under the same environmental conditions. The morphological and/ or physiological characteristics may vary somewhat with variation in the environment (such as temperature, light intensity, day length, humidity, soil, fertilizer use), which is why a comparison under the same environmental conditions is preferred. Colors can best be measured using the Royal Horticultural Society (RHS) Chart.

In another aspect, the disclosure provides a method of producing a plant derived from a cucumber variety NUN 13088 CUL, comprising crossing the plant of variety NUN 13088 CUL either as a male or female parent with a second cucumber plant or selfing cucumber variety NUN 13088 CUL or vegetatively propagating cucumber NUN 13088 CUL and collecting seeds from said crossing or selfing or regenerating a whole plant from the vegetable cell—or tissue culture. Also provided are seeds and/or plants obtained by this method. All plants produced using cucumber variety NUN 13088 CUL as a parent are within the scope of the disclosure including plant parts derived from cucumber variety NUN 13088 CUL.

In further aspects, the method comprises growing a progeny plant of a subsequent generation and crossing the progeny plant of a subsequent generation with itself or a second plant and repeating the steps for additional 3-10 generations to produce a plant derived from cucumber variety NUN 13088 CUL. The plant derived from cucumber variety NUN 13088 CUL may be an inbred line and the aforementioned repeating crossing steps may be defined as comprising sufficient inbreeding to produce the inbred line. By selecting plants having one or more desirable traits of the line as well as potentially other selected traits.

The disclosure provides for methods of producing plants which retain all the morphological and physiological characteristics of the plant described herein. The disclosure also provides for methods of producing a plant comprising all but 1, 2, or 3 or more of the morphological and physiological characteristics of cucumber variety NUN 13088 CUL (e.g., as listed in Tables 1-3), but which are still genetically closely related to said variety. The relatedness can, for example, be determined by fingerprinting techniques (e.g., making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to cucumber variety NUN 13088 CUL if its DNA fingerprint is at least 80%, 90%, 95% or 98% identical to the fingerprint of cucumber variety NUN 13088 CUL. In a particular aspect, AFLP markers are used for DNA fingerprinting (see, e.g., Vos et al. 1995, Nucleic Acid Research 23: 4407-4414). A closely related plant may have a Jaccard's Similarity index of at least about 0.8, preferably at least about 0.9, 0.95, 0.98 or more (see, e.g., Parvathaneni et al., J. Crop Sci. Biotech. 2011 (March) 14 (1): 39-43). The disclosure also provides a plant and a variety obtained or selected by applying these methods on cucumber variety NUN 13088 CUL. Such a plant may be produced by crossing and/or selfing, or alternatively, a plant may simply be identified and selected amongst plants of said variety, or progeny of said variety, e.g., by identifying a variant within cucumber variety NUN 13088 CUL or within progeny of said variety (e.g., produced by selfing) which variant differs from cucumber variety NUN 13088 CUL in one, two, or three of the morphological and/or physiological characteristics (e.g., in one, two, or three distinguishing characteristics), e.g. those listed in Tables 1-3. In another aspect, the disclosure provides a cucumber plant having a Jaccard's Similarity index with cucumber variety NUN 13088 CUL of at least 0.8, e.g., at least 0.85, 0.9, 0.95, 0.98 or even at least 0.99.

In some aspects, the disclosure provides a cucumber plant comprising genomic DNA having at least 95%, 96%, 97%, 98% or 99% Sequence identity compared to the genomic DNA Sequence of a plant of variety NUN 13088 CUL as deposited under Accession Number NCIMB 44043. In some aspects, the cucumber plant further comprises all or all but 1, 2, or 3 of the morphological and physiological characteristics of cucumber variety NUN 13088 CUL (e.g. as listed in Tables 1-3). In other aspects, the cucumber plant is a hybrid derived from a seed or plant of variety NUN 13088 CUL. In another aspects the cucumber plant comprises the physiological and morphological characteristics of cucumber variety NUN 13088 CUL.

For the purpose of this disclosure, the "Sequence identity" of nucleotide Sequences, expressed as a percentage, refers to the number of positions in the two optimally aligned Sequences which have identical residues (×100) divided by the number of positions compared. A gap, i.e., a position in the pairwise alignment where a residue is present in one Sequence but not in the other, is regarded as a position with non-identical residues. A pairwise global Sequence alignment of two nucleotide Sequences is found by aligning the two Sequences over the entire length according to the Needleman and Wunsch global alignment algorithm described in Needleman and Wunsch, 1970, J. Mol. Biol. 48(3):443-53). A full implementation of the Needleman-Wunsch global alignment algorithm is found in the needle program in The European Molecular Biology Open Software Suite (see, e.g., EMBOSS, Rice et al., Trends in Genetics June 2000, vol. 16, No. 6. pp. 276-T77).

In one aspect, the plant of cucumber variety NUN 13088 CUL may also be mutated (by e.g., irradiation, chemical mutagenesis, heat treatment, etc.) and mutated seeds or plants may be selected in order to change one or more characteristics of said variety. Methods such as TILLING (Targeting Induced Local Lesions in Genomes) may be applied to cucumber populations in order to identify mutants.

Similarly, cucumber variety NUN 13088 CUL may be transformed and regenerated, whereby one or more chimeric genes are introduced into the variety or into a plant comprising all but 1, 2, 3, or more of the morphological and physiological characteristics (e.g., as listed in Tables 1-3). Many useful traits can be introduced into cucumber variety 13088 CUL by e.g., crossing cucumber variety NUN 13088 CUL with a transgenic cucumber plant comprising desired transgene, as well as by directly introducing a transgene into cucumber variety NUN 13088 CUL by genetic transformation techniques.

Transformation can be carried out using standard methods, such as *Agrobacterium tumefaciens* mediated transformation or biolistics, followed by selection of the transformed cells and regeneration into plants. A desired trait (e.g., gene(s) conferring pest or disease resistance, herbicide, fungicide or insecticide tolerance, etc.) can be introduced into cucumber variety NUN 13088 CUL, or progeny of said variety, by transforming said variety or progeny of said variety with a transgene that confers the desired trait, wherein the transformed plant retains all or all but one, two or three of the phenotypic and/or morphological and/or physiological characteristics of cucumber variety NUN 13088 CUL or the progeny of said variety and contains the desired trait. In another aspect, the transformation or mutation confers a trait wherein the trait is the desired trait is yield, size, compactness, dry matter content, fruit quality, enhanced nutritional quality, post-harvest quality, storage properties, color, male sterility, herbicide tolerance, insect resistance, pest resistance, disease resistance, Powdery mildew resistance without necrosis, environmental stress tolerance, modified carbohydrate metabolism, modified protein metabolism, or ripening.

Any pest or disease resistance genes may be introduced into the plant of variety NUN 13088 CUL, progeny of said variety or into a plant comprising all but 1, 2, or 3 or more of the morphological and physiological characteristics of cucumber variety NUN 13088 CUL (e.g., as listed in Tables 1-3). Resistance to one or more of the following diseases or pests may be introduced into plants described herein: Angular Leaf Spot (*Pseudomonas lachrymans*), Anthracnose Race 1 (*Colletotrichum lagenaria*), Anthracnose Race 2, Bacterial Wilt (*Erwinia tracheiphilus*), Cucumber Scab (Gummosis) (*Cladosporium cucumerinum*), Downy Mildew (*Pseudoperonospora cubensis*), Powdery Mildew (*Erysiphe chicoracearum*), Alternaria Leaf Blight (*Alternaria cucumerina*), Target Spot (*Corynespora cassiicola*), Cucumber Rust, Root Rot, Crown Blight, Verticillum Wilt, Sulphur Burn, *Fusarium oxysporum* f.sp. *cucumerinum, Fusarium* Wilt Race2, Root Knot (Nematode), Anthracnose, and/or Squash Mosaic. Other resistances, against pathogenic viruses (e.g., Cucumber Mosaic Virus (CMV), Cucumber Yellow Mottle Mosaic Virus (CYMMV), Cucumber Green Mottle Mosaic Virus (CGMMV), Cucumber Aucuba Mosaic Virus (CAMV), Muskmelon Mosaic Virus (MMV), Cucumber Vein Yellowing Virus (CVYV), Cucurbit Yellow Stunting Disorder Virus (CYSDV), Watermelon Mosaic Virus (WMV), Papaya Ring Spot Virus (PRSV), Zucchini Mosaic Virus (ZMV)), fungi, bacteria, nematodes, insects, or other pests may also be introduced.

Genetic transformation may, therefore, be used to insert a selected transgene into the cucumber plants of the disclosure described herein or may, alternatively, be used for the preparation of transgenic cucumber plants which can be used as a source of the transgene(s), which can be introduced into cucumber variety NUN 13088 CUL by e.g., backcrossing. A genetic trait which has been engineered into the genome of a particular cucumber plant may then be moved into the genome of another cucumber plant (e.g., another variety) using traditional breeding techniques which are well-known in the art. For example, backcrossing is commonly used to move a transgene from a transformed cucumber variety into an already developed cucumber variety and the resulting backcross conversion plant will then comprise the transgene(s). Any DNA Sequences, whether from a different species or from the same species, which are inserted into the genome using transformation, are referred to herein collectively as "transgenes." A "transgene" also encompasses antisense, or sense and antisense Sequences capable of gene silencing. Thus, the disclosure also related to transgenic plants of cucumber variety NUN 13088 CUL. In some aspects, a transgenic plant of cucumber variety NUN 13088 CUL may contain at least one transgene but could also contain at least 1, 2, 3, 4, or more transgenes.

Plant transformation involves the construction of an expression vector which will function in plant cells. Such a vector comprises DNA comprising a gene under control of, or operatively linked to a regulatory element active in plant cells (e.g., promoter). The expression vector may contain one or more such operably linked gene/regulatory element combinations. The vector may be in the form of a plasmid and can be used alone or in combination with other plasmids to provide transformed cucumber plants using transformation methods to incorporate transgenes into the genetic material of the cucumber plant(s). transformation can be carried out using standard methods, such as *Agrobacterium tumefaciens* mediated transformation, electroporation, biolistics particle delivery stem, or microprojectile bombardment, followed by selection of the transformed cells and regeneration into plants.

Plants can also be genetically engineered, modified, or manipulated to express various phenotypes of horticultural interest. Through the transformation of cucumber, the expression of genes can be altered to enhance disease resistance, insect resistance, herbicide resistance, stress tolerance, horticultural quality, and other traits. Transformation can also be used to insert DNA Sequences which control or help control male sterility or fertility restoration. DNA Sequences native to cucumber as well as non-native DNA Sequences can be transformed into cucumber and used to alter levels of native or non-native proteins. Reduction of the specific activity of specific genes (also known as gene silencing or gene suppression) is desirable for several aspects of genetic engineering in plants.

Genome editing is another method recently developed to genetically engineer plants. Specific modification of chromosomal loci or targeted mutation can be done through Sequence-specific nucleases (SSNs) by introducing a targeted DNA double strand break in the locus to be altered. Examples of SSNs that been applied to plants are: finger nucleases (ZFNs), transcription activator-like effector nucleases (TALENs), engineered homing endonucleases or meganucleases, and clustered regularly interspaced short palindromic repeats (CRISPR)/(CRISPR associated protein 9 (Cas9)), see, e.g., Songtad, et. al., Critical Reviews in Plant Sciences, 2017, 36:1, 1-23.

Thus, the disclosure also provides a method of producing a cucumber plant having a desired trait comprising mutating the plant or plant part of variety NUN 13088 CUL and selecting a plant with the desired trait, wherein the mutated plant retains all or all but one, two, or three of the physiological and morphological characteristics of cucumber variety NUN 13088 CUL, optionally as described Tables 1-3, and contains the desired trait and wherein a representative sample of seed of variety NUN 13088 CUL has been deposited under Accession Number NCIMB 44043. In a further aspect, the desired trait is yield, size, compactness, dry matter content, fruit quality, enhanced nutritional quality, post-harvest quality, storage properties, color, male sterility, herbicide tolerance, insect resistance, pest resistance, disease resistance, Powdery mildew resistance without necrosis, environmental stress tolerance, modified carbohydrate metabolism, modified protein metabolism, or ripening.

In one aspect, the disclosure provides a method for inducing a mutation in cucumber variety NUN 13088 CUL comprising:

a. exposing the seed, plant, plant part, or cell of cucumber variety NUN 13088 CUL to a mutagenic compound or to radiation, wherein a representative sample of seed of said cucumber variety is deposited under Accession Number NCIMB 44043;

b. selecting the seed, plant, plant part, or a cell of cucumber variety NUN 13088 CUL, having a mutation; and c. optionally growing and/or multiplying the seed, plant, plant part, or cell of cucumber variety NUN 13088 CUL, having the mutation.

The disclosure also provides a method of producing a cucumber plant having a desired trait, wherein the method comprises transforming the cucumber plant with a transgene that confers the desired trait, wherein the transformed plant otherwise retains all of the physiological and morphological characteristics of the cucumber variety NUN 13088 CUL and contains the desired trait. Thus, a transgenic cucumber plant is provided which is produced by the method described above, wherein the plant otherwise has all of the physiological and morphological characteristics of cucumber variety NUN 13088 CUL and the desired trait.

In another aspect, the disclosure provides a method of producing a progeny of cucumber variety NUN 13088 CUL, further comprising a desired trait, said method comprising transforming the plant of cucumber variety NUN 13088 CUL with a transgene that confers the desired trait and/or crossing the plant of cucumber variety NUN 13088 CUL with a transgenic cucumber plant comprising a desired transgene so that the genetic material of the progeny that resulted from the cross contains the desired transgene(s). Also encompassed is the progeny produced by this method.

A desired trait (e.g., gene(s)) conferring pest or disease resistance, or tolerance for protection, etc. can be introduced into cucumber plant variety NUN 13088 CUL, or progeny of said variety, by transforming said variety or progeny of said variety with a transgene that confers the desired trait, wherein the transformed plant otherwise retains all or all but one, two, or three of the physiological and morphological characteristics of cucumber variety NUN 13088 CUL, and contains the desired trait. In another aspect, the transformation or mutation confers a trait wherein the trait is yield, size, compactness, dry matter content, fruit quality, enhanced nutritional quality, post-harvest quality, storage properties, color, male sterility, herbicide tolerance, insect resistance, pest resistance, disease resistance, Powdery mildew resistance without necrosis, environmental stress tolerance, modified carbohydrate metabolism, modified protein metabolism, or ripening. In a particular aspect, the specific transgene may be any known in the art or listed herein, including a polynucleotide Sequence conferring resistance to imidazolinone, sulfonylurea, glyphosate, glufosinate, triazine, benzonitrile, cyclohexanedione, phenoxy proprionic acid and L-phosphinothricin or a polynucleotide conferring resistance to Angular Leaf Spot (*Pseudomonas lachrymans*), Anthracnose Race 1 (*Colletotrichum lagenaria*), Anthracnose Race 2, Bacterial Wilt (*Erwinia tracheiphilus*), Cucumber Scab (Gummosis) (*Cladosporium cucumerinum*), Downy Mildew (*Pseudoperonospora cubensis*), Powdery Mildew (*Erysiphe chicoracearum*), *Alternaria* Leaf Blight (*Alternaria cucumerina*), Target Spot (*Corynespora cassiicola*), Cucumber Rust, Root Rot, Crown Blight, Verticillum Wilt, Sulphur Burn, *Fusarium oxysporum* f sp. *cucumerinum, Fusarium* Wilt Race2, Root Knot (Nematode), Anthracnose, and/or Squash Mosaic. Other resistances, against pathogenic viruses (e.g., Cucumber Mosaic Virus (CMV), Cucumber Yellow Mottle Mosaic Virus (CYMMV), Cucumber Green Mottle Mosaic Virus (CGMMV), Cucumber Aucuba Mosaic Virus (CAMV), Muskmelon Mosaic Virus (MMV), Cucumber Vein Yellowing Virus (CVYV), Cucurbit Yellow Stunting Disorder Virus (CYSDV), Watermelon Mosaic Virus (WMV), Papaya Ring Spot Virus (PRSV), Zucchini Mosaic Virus (ZMV)), fungi, bacteria, nematodes, insects, or other pests may also be introduced.

By crossing and/or selfing, (one or more) single traits may be introduced into cucumber variety NUN 13088 CUL (e.g., using backcrossing breeding schemes), while retaining the morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g., dominant or recessive) and one or more QTLs (quantitative trait loci) may be transferred into cucumber variety NUN 13088 CUL by breeding with said variety.

Alternatively, a single trait converted plant or single locus converted plant of variety NUN 13088 CUL may be produced by (i) genetically transforming or mutating cells of NUN 13088 CUL; (ii) growing the cells into a plant; and (iii) optionally selecting a plant that contains the desired single locus conversion. The skilled person is familiar with various techniques for genetically transforming a single locus in a plant cell, or mutating said cells.

In another aspect the disclosure provides a method of introducing a single locus conversion, a single trait conversion, or a desired trait into cucumber variety NUN 13088

CUL, comprising introducing a single locus conversion, a single trait conversion, or a desired trait in at least one of the parents of cucumber variety NUN 13088 CUL, and crossing the converted parent with the other parent of cucumber variety NUN 13088 CUL to obtain seed of said variety.

In another aspect, the step of introducing a single locus conversion, a single trait conversion, or a desired trait in at least one of the parents comprises:

a. crossing the parental line of cucumber variety NUN 13088 CUL with a second cucumber plant comprising the single locus conversion, the single trait conversion, or the desired trait;

b. selecting F1 progeny plants that contain the single locus conversion, the single trait conversion, or the desired trait;

c. crossing said selected progeny plants of step b) with the parental line of step a) to produce a backcross progeny plant;

d. selecting backcross progeny plants comprising the single locus conversion, the single trait conversion, or the desired trait and otherwise all or all but one, two or three of the morphological and physiological characteristics the parental line of step a) to produce selected backcross progeny plants; and e. optionally repeating steps c) and d) one or more times in succession to produce selected second, third or fourth or higher backcross progeny plants comprising the single locus conversion, the single trait conversion or the desired trait and otherwise all or all but one, two or three of the morphological and physiological characteristics the parental line of step a) to produce selected backcross progeny plants, when grown in the same environmental conditions.

The disclosure further relates to plants obtained by this method.

In another aspect, the step of introducing a single locus conversion, a single trait conversion, or a desired trait in at least one of the parents comprises:

a. obtaining a cell or tissue culture of cells of the parental line of cucumber variety NUN 13088 CUL;

b. genetically transforming or mutating said cells;

c. growing the cells into a plant; and d. optionally selecting plants that contain the single locus conversion, the single trait conversion or the desired trait.

In another aspect, the disclosure provides a method of introducing a single locus conversion, a single trait conversion or a desired trait into cucumber variety NUN 13088 CUL comprising:

a. obtaining a combination of a parental lines of cucumber variety NUN 13088 CUL, optionally through reverse synthesis of breeding lines;

b. introducing a single locus conversion, a single trait conversion, or a desired trait in at least one of the parents of step a); and c. crossing the converted parent with the other parent of step a to obtain seed of cucumber variety NUN 13088 CUL.

In another method, the step of introducing a single locus conversion, single trait conversion, or a desired trait in at least one of the parents comprises genetically transforming or mutating cells the parental line of cucumber variety NUN 13088 CUL, growing the cells into a plant, and optionally selecting plants that contain the single locus conversion, the single trait conversion, or the desired trait.

In any of the above methods, where the single locus conversion concerns a trait, the trait may be yield or pest resistance or disease resistance. In one aspect, the trait is disease resistance and the resistance is conferred to Angular Leaf Spot (*Pseudomonas lachrymans*), Anthracnose Race 1 (*Colletotrichum lagenaria*), Anthracnose Race 2, Bacterial Wilt (*Erwinia tracheiphilus*), Cucumber Scab (Gummosis) (*Cladosporium cucumerinum*), Downy Mildew (*Pseudoperonospora cubensis*), Powdery Mildew (*Erysiphe chicoracearum*), *Alternaria* Leaf Blight (*Alternaria cucumerina*), Target Spot (*Corynespora cassiicola*), Cucumber Rust, Root Rot, Crown Blight, Verticillum Wilt, Sulphur Burn, *Fusarium oxysporum* fsp. *cucumerinum, Fusarium* Wilt Race 2, Root Knot (Nematode), Anthracnose, and/or Squash Mosaic. Other resistances, against pathogenic viruses, e.g., Cucumber Mosaic Virus (CMV), Cucumber Yellow Mottle Mosaic Virus (CYMMV), Cucumber Green Mottle Mosaic Virus (CGMMV), Cucumber Aucuba Mosaic Virus (CAMV), Muskmelon Mosaic Virus (MMV), Cucumber Vein Yellowing Virus (CVYV), Cucurbit Yellow Stunting Disorder Virus (CYSDV), Watermelon Mosaic Virus (WMV), Papaya Ring Spot Virus (PRSV), Zucchini Mosaic Virus (ZMV), fungi, bacteria, nematodes, insects, or other pests may also be introduced.

The disclosure also provides a plant having one, two, or three physiological or morphological characteristics which are different from those of cucumber variety NUN 13088 CUL, and which otherwise has all the physiological and morphological characteristics of said variety, wherein a representative sample of seed of variety has been deposited under Accession Number NCIMB 44043. In particular, variants which differ from cucumber variety NUN 13088 CUL in none, one, two, or three of the characteristics mentioned in Tables 1-3 are encompassed.

The disclosure also provides a cucumber plant comprising at least a first set of the chromosomes of cucumber variety NUN 13088 CUL, a sample of seed of said variety having been deposited under Accession Number NCIMB 44043; optionally further comprising a single locus conversion, wherein said plant has essentially all of the morphological and physiological characteristics of the plant comprising at least a first set of the chromosomes of said variety. In another aspect, this single locus conversion confers a trait wherein the trait yield, size, compactness, dry matter content, fruit quality, enhanced nutritional quality, post-harvest quality, storage properties, color, male sterility, herbicide tolerance, insect resistance, pest resistance, disease resistance, Powdery mildew resistance without necrosis, environmental stress tolerance, modified carbohydrate metabolism, modified protein metabolism, or ripening.

In one aspect, the disclosure provides for a haploid plant and/or a doubled haploid plant of variety NUN 13088 CUL, or of a plant having all but one, two, or three physiological or morphological characteristics of cucumber variety NUN 13088 CUL, or progeny of said variety. Haploid and doubled haploid (DH) plants can, for example, be produced by cell or tissue culture and chromosome doubling agents and regeneration into a whole plant. In a method for DH production, chromosome doubling may be induced using known methods, such as colchicine treatment or the like. In one aspect, the method comprises inducing a cell or tissue culture with a chromosome doubling agent and regenerating the cells or tissues into a whole plant.

In another aspect, the disclosure comprises a method for making doubled haploid cells of cucumber variety NUN 13088 CUL, comprising making doubled haploid cells from haploid cells from the plant or plant part of cucumber variety NUN 13088 CUL with a chromosome doubling agent such as colchicine treatment (see, e.g., Nikolova and Niemirow-icz-Szczytt (1996) Acta Soc Bot Pol 65:311-317).

In yet another aspect, the disclosure provides for haploid plants and/or doubled haploid plants derived from cucumber variety NUN 13088 CUL that, when combined, make a set of parents of cucumber variety NUN 13088 CUL. The haploid plant and/or the doubled haploid plant of variety NUN 13088 CUL can be used in a method for generating parental lines of cucumber variety NUN 13088 CUL.

In one aspect, the disclosure relates to a method of producing a combination of parental lines of the plant of variety NUN 13088 CUL, comprising making doubled haploid cells from haploid cells from said plant or seed of that plant; and optionally crossing these parental lines to produce and collecting seeds. In another aspect, the disclo-sure relates to a combination of parental lines produced by this method. In still another aspect, the combination of parental lines can be used to produce a seed or plant of variety NUN 13088 CUL when these parental lines are crossed. In still another aspect, the disclosure relates to a combination of parental lines from which a seed or plant having all physiological and/or morphological characteris-tics of cucumber variety NUN 13088 CUL, e.g., when the numerical characteristics are determined at the 5% signifi-cance level and identical (same type or degree) for non-numerical characteristics for plants grown under the same environmental conditions.

The disclosure also provides a method for producing parental lines for hybrid variety NUN 13088 CUL compris-ing: genetically characterizing a doubled haploid line from cucumber variety NUN 13088 CUL to determine whether one or more genetic markers are present in a first homozy-gous form or in a second homozygous form in said line, wherein one or more genetic markers are present in a heterozygous form in cucumber variety NUN 13088 CUL; and selecting at least one pair of doubled haploid lines that have complementary alleles for one or more genetic mark-ers, wherein each member of the pair is suitable as a parental line for a hybrid organism, optionally this method further comprises defining a set of genetic markers present in a heterozygous form in cucumber variety NUN 13088 CUL; and producing doubled haploid lines from cucumber variety NUN 13088 CUL. Doubled haploid lines generated as described herein can be used in such method.

A combination of a male and a female parental line of cucumber variety NUN 13088 CUL can also be generated, for example, through reverse synthesis of breeding lines.

Using methods known in the art such as "reverse synthe-sis of breeding lines" or "reverse breeding," it is possible to produce parental lines for a hybrid plant such as cucumber variety NUN 13088 CUL. A skilled person can take any individual heterozygous plant (called a "phenotypically superior plant" in Example 2 of US 2015/0245570; cucum-ber variety NUN 13088 CUL is such a plant) and generate a combination of parental lines (reverse breeding parental lines) that, when crossed, produce the variety NUN 13088 CUL. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable prog-eny plants in one generation, or in a limited number of inbred cycles. Such a method is known from US 2015/0245570 or from Wijnker et al., Nature Protocols Volume: 9, Pages: 761-772 (2014) DOI: doi:10.1038/nprot.2014.049. Thus, the disclosure provides a method for producing parental lines for a hybrid organism (e.g., cucumber variety NUN 13088 CUL), comprising in one aspect: a) defining a set of genetic markers present in a heterozygous form (H) in a partially heterozygous starting organism; b) producing doubled haploid lines from spores of the starting organism; c) genetically characterizing the doubled haploid lines thus obtained for the said set of genetic markers to determine whether they are present in a first homozygous form (A) or in a second homozygous form (B); and d) selecting at least one pair of doubled haploid lines that have complementary alleles for at least a subset of the genetic markers, wherein each member of the pair is suitable as a parental line for the hybrid organism.

In another aspect, the method for producing parental lines for hybrid organisms, e.g., of cucumber variety NUN 13088 CUL, which when crossed reconstitute the genome of cucumber variety NUN 13088 CUL, comprising:
   a. defining a set of genetic markers that are present in a heterozygous form (H) in a partially heterozygous starting organism;
   b. producing at least one further generation from the starting organism by self-pollination (e.g., F2 or F3 generation);
   c. selecting at least one pair of progeny organisms in which at least one genetic marker from the set is present in a complementary homozygous forms (B vs. A, or A vs. B); and
   d. optionally repeating steps b) and c) until at least one pair of progeny organisms that have complementary alleles for at least a subset of the genetic markers has been selected as parental lines for a hybrid.

The disclosure also provides methods for determining the identity of parental lines of plants described herein, in particular the identity of the female line. US 2015/0126380, relates to a non-destructive method for analyzing maternal DNA of a seed. In this method, the DNA is dislodged from the seed coat surface and can be used to collect information on the genome of the maternal parent of the seed. This method for analyzing maternal DNA of a seed comprises contacting a seed with a fluid to dislodge DNA from the seed coat surface, and analyzing the DNA thus dislodged from the seed coat surface using methods known in the art. The skilled person is thus able to determine whether a seed has grown on a plant of variety NUN 13088 CUL or is a progeny of said variety, because the seed coat of the seed is a maternal tissue genetically identical to cucumber variety NUN 13088 CUL. In one aspect, the disclosure relates to a seed coat comprising maternal tissue of cucumber variety NUN 13088 CUL. In another aspect, the disclosure relates to a cucumber seed comprising a maternal tissue of cucum-ber variety NUN 13088 CUL. In another particular aspect, the disclosure provides for a method of identifying the female parental line of cucumber variety NUN 13088 CUL by analyzing the seed coat of a seed of that variety. In another aspect, the skilled person can determine whether a seed is grown on cucumber variety NUN 13088 CUL by analyzing the seed coat or another maternal tissue of said seed.

In another aspect, the disclosure provides a method of determining the genotype of a plant described herein com-prising detecting in the genome (e.g., a sample of nucleic acids) of the plant at least a first polymorphism or an allele. The skilled person is familiar with many suitable methods of genotyping, detecting a polymorphism or detecting an allele including SNP (single Nucleotide Polymorphism) genotyp-ing, restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain aspects, comprise detecting a plurality of polymorphisms in the genome of the plant, for example, by obtaining a sample of nucleic acid from a plant and detecting in said nucleic acids a plurality of polymorphisms. The method may further comprise storing the results of the step of detecting the plurality of polymorphisms on a computer readable medium.

Also provided is a plant part obtainable from variety NUN 13088 CUL or from progeny of said variety or from a plant having all but one, two or three physiological and/or morphological characteristics which are different from those of cucumber variety NUN 13088 CUL, or from a vegetatively propagated plant of variety NUN 13088 CUL (or from its progeny or from a plant having all or all but one, two or three physiological and/or morphological characteristics which are different from those of cucumber variety NUN 13088 CUL, wherein the plant part is a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed-coat or another maternal tissue which is part of a seed grown on cucumber variety NUN 13088 CUL or a hypocotyl, a cotyledon, a scion, a stock, a rootstock, a pistil, an anther, or a flower or a part thereof.

Such a plant part of variety NUN 13088 CUL can be stored and/or processed further. The disclosure thus, provides for a food or a feed product comprising one or more of such parts, such as canned, chopped, cooked, roasted, in a sauce, in a sandwich, pasted, puréed or concentrated, juiced, frozen, dried, pickled, or powdered cucumber fruit from cucumber variety NUN 13088 CUL or from progeny of said variety, or from a derived variety, such as a plant having all but one, two, or three physiological and/or morphological characteristics of cucumber variety NUN 13088 CUL. Preferably, the plant part is a cucumber fruit or part thereof and/or an extract from a fruit of the plant described herein comprising at least one cell of cucumber variety NUN 13088 CUL. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

In another aspect, the disclosure provides for a cucumber fruit of variety NUN 13088 CUL, or a part of a fruit of said variety. The fruit can be in any stage of maturity, for example, immature or mature. In another aspect, the disclosure provides for a container comprising or consisting of a plurality of harvested cucumber fruits or parts of fruits of said variety, or fruits of progeny thereof, or fruits of a derived variety. Marketable fruits are generally sorted by size and quality after harvest.

In another aspect, the plant, plant part, or seed of cucumber variety NUN 13088 CUL is inside one or more containers. For example, the disclosure provides containers such as cans, boxes, crates, bags, cartons, Modified Atmosphere Packaging, films (e.g., biodegradable films), etc. comprising a plant or a plant part (fresh and/or processed) or a seed of cucumber variety NUN 13088 CUL. In a particular aspect, the container comprises a plurality of seeds of cucumber variety NUN 13088 CUL, or a plurality of plant parts of cucumber variety NUN 13088 CUL. The seeds may be disinfected, primed and/or treated with various compounds, such as seed coatings or crop protection compounds. The seed produces a plant of variety NUN 13088 CUL.

Cucumbers may also be grown for use as rootstocks (stocks) or scions. Typically, different types of cucumbers are grafted to enhance disease resistance, which is usually conferred by the rootstock, while retaining the horticultural qualities usually conferred by the scion. It is not uncommon for grafting to occur between cultivated cucumber varieties and related cucumber species. Methods of grafting and vegetative propagation are well-known in the art.

In another aspect, the disclosure provides to a plant comprising a rootstock or scion of cucumber variety NUN 13088 CUL.

REFERENCES

Naktuinbouw, "Calibration Book for Cucumber & Gherkin," Netherlands, December 2010.

UPOV, "Guidelines for the Conduct of Tests for Distinctness, Uniformity and Stability", TG/61/7, March 2019.

US Department of Agriculture, "Objective Description of Variety Cucumber (*Cucumis sativus* L.)", June 2015.

Colijn-Hooymans, J. C., et. al., "Competence for Regeneration of Cucumber Cotyledons is Restricted to Specific Developmental Stages", Plant Cell, Tissue and Organ Culture, 1994, vol. 39, pp. 211-217.

Needleman, S. B., et. al., "A General Method Applicable to the Search for Similarities in the Amino Acid Sequence of Two Proteins", Journal of Molecular Biology, 1970, vol. 48(3), pp. 443-53.

Nikolova, V., et. al., "Diploidization of Cucumber (*Cucumis sativus* L.) Haploids by Colchini Treatment", Acta Societas Botanicorum Poloniae, 1996, vol. 65, pp. 311-317.

Parvathaneni, R. K., et al., "Fingerprinting in Cucumber and Melon (*Cucumis* spp.) genotypes Using Morphological and ISSR Markers", Journal of Crop Science and Biotechnology, 2011, vol. 14, no. 1, pp. 39-43. DOI No. 10.1007/s12892-010-0080-1.

Rice, P., et al., "EMBOSS: The European Molecular Biology Open Software Suite", Trends in Genetics, 2000, vol. 16, Issue 6. pp. 276-277.

Sang-Gu, K., et. al., "Callus growth and Plant Regeneration in Diverse Cultivars of Cucumber (*Cucumis sativus* L.), Plant Cell, Tissue and Organ Culture, 1998, vol. 12, pp. 67-74.

Sarreb, D. A., et. al., "Comparison of Triploid and Diploid Cucumber in Long-term Liquid Cultures," Plant Cell, Tissue and Organ Culture, 2002, vol. 71-3, pp. 231-235.

Schrader, et. al., University of California Agriculture and Natural Resources, Publication 8050, 2002, 1-8

Vidaysky, F., et. al., "Tomato Breeding Lines Resistant and Tolerant to Tomato Yellow Leaf Curl Virus Issued from *Lycopersicum hirsutum*", The American Phytopathology Society, 1998, vol. 88, no. 9, pp. 910-914.

Vos, P., et al., "AFLP: A New Technique for DNA Fingerprinting", Nucleic Acids Research, 1995, vol. 23(21), pp. 4407-4414.

Wijnker, E., et al., "Hybrid Recreation by Reverse breeding in *Arabidopsis thaliana*", Nature Protocols, 2014, vol. 9, pp. 761-772. DOI: doi: 10.1038/nprot.2014.049.

U.S. Pat. No. 4,822,949

U.S. Pat. No. 5,349,128

U.S. Pat. No. 5,492,827

U.S. Pat. No. 6,084,152

US 2015/0126380

US 2015/0245570

US 2018/0054990

US 2017/0335339

Development of Cucumber Variety NUN 13088 CUL

The hybrid variety NUN 13088 CUL was developed from a cross between female parent CU1279 and male parent line CU1883. Both female and male parental lines are proprietary inbred lines and are not publicly available. The female and male parents were crossed to produce hybrid (F1) seeds of cucumber variety NUN 13088 CUL. The seeds of cucumber variety NUN 13088 CUL can be grown to produce hybrid plants and parts thereof (e.g., cucumber fruit). The hybrid variety NUN 13088 CUL can be propagated by seeds or vegetatively.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that cucumber variety NUN 13088 CUL is uniform and stable.

Deposit Information

A total of 625 seeds of the hybrid variety NUN 13088 CUL was made and accepted according to the Budapest Treaty by Nunhems B. V. on Sep. 28, 2022, at the NCIMB Ltd., Ferguson Building, Craibstone Estate, Bucksburn, Aberdeen AB21 9YA, United Kingdom (NCIMB). The deposit has been assigned Accession Number NCIMB 44043. A statement indicating the viability of the sample has been provided. A deposit of cucumber variety NUN 13088 CUL and of the male and female parent line is also maintained at Nunhems B. V. The seed lot number for cucumber variety NUN 13088 CUL is 31852502002.

The deposit will be maintained for a period of 30 years, or 5 years after the most recent request, or for the enforceable life of the patent whichever is longer and will be replaced if it ever becomes nonviable during that period. Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. Applicant does not waive any rights granted under this patent on this application or under the Plant Variety Protection Act (7 U.S.C. § 2321 et seq.). Accordingly, the requirements of 37 CFR § 1.801-1.809 have been satisfied.

Characteristics of Cucumber Variety NUN 13088 CUL

The most similar variety to NUN 13088 CUL refers to variety Verdon, a commercial variety from Rijk Zwaan.

In Table 1, the characteristics of cucumber variety NUN 13088 CUL are shown based on a trial in Canada in 2022 under high tech conditions (i.e., greenhouse). In Tables 2 and 3, a comparison between cucumber variety NUN 13088 CUL and the Reference Variety are described based on a trial Leamington, Ontario, Canada in 2023 under low wire commercial greenhouse. Plants are trained upward and then folded over wires between 8 and 10 feet high.

One replication of 30 plants per variety, from which at least 15 plants or plant parts were randomly selected and were used to measure the characteristics. For numerical characteristics, averages were calculated. For non-numerical characteristics, the type or degree were determined. Similarity and differences between two different plant lines or varieties can be determined by comparing the number of morphological and/or physiological characteristics that are the same (i.e., statistically not significantly different) or that are different (i.e., statistically significantly different) between the two plant lines or varieties using plants grown under the same environmental conditions. Preferably, a numerical characteristic is considered to be "the same" when the value for a numeric characteristic is not significantly different at the 1% (p<0.01) or 5% (p<0.05) significance level, using a T-test, a standard method known to the skilled person. Preferably, non-numerical or "degree" or "type" characteristics are considered "the same" when the values have the same "degree" or "type" when scored using USDA and/or UPOV descriptors if the plants are grown under the same environmental conditions. In one aspect, a statistical analysis using the T-test at 5% significance level is provided (see, Tables 5-15).

In another aspect, the disclosure provides a cucumber plant having all of the physiological and morphological characteristics of cucumber variety NUN 13088 CUL as presented in Tables 1-3 when grown under the same environmental conditions, wherein a representative sample of seed of said cucumber variety NUN 13088 CUL has been deposited under Accession Number NCIMB 44043.

TABLE 1

| Characteristics of Cucumber Variety NUN 13088 CUL | |
| --- | --- |
| Characteristics | Application Variety (NUN 13088 CUL) |
| Type: | |
| Predominant usage: | Fresh Market |
| slicing (fresh market), pickling | |
| Predominant culture: | Greenhouse |
| outdoor, greenhouse | |
| Area of best adaptation in the US: | All areas |
| North, South, Most Areas | |
| Maturity: | |
| Days from seedling to market maturity | 19 days |
| Cotyledon: | |
| Bitterness: | Absent |
| absent, present | |
| Plant: | |
| Habit: | Vine |
| bush, semi-bush, vine | |
| Growth: | Indeterminate |
| determinate, indeterminate | |
| Sex: | Gynoecious |
| andromonoecious, monoecious, primarily | |
| gynoecious, 100% gynoecious | |
| Number of female flowers per node: | Predominately one or two |
| Predominantly one, Predominantly one or two, Predominantly two, Predominantly two or three, Predominantly three or four, Predominantly four or five, Predominantly more than five | |
| Time of development of flowers (80% of plants with at least one flower): | Very Early |
| very early, very early to early, early, early to medium, medium, medium to late, late, late to very late, very late | |
| Ovary: | |
| Color of vestiture: | White |
| white, black | |
| Main Stem: | |
| Length of internode: | Short |
| very short, short, medium, long, very long | |
| Stem form: | Grooved |
| grooved, ridged; smooth, round | |

TABLE 1-continued

Characteristics of Cucumber Variety NUN 13088 CUL

| Characteristics | Application Variety (NUN 13088 CUL) |
| --- | --- |
| Fruit at edible maturity: | |
| Fruit length: | Medium to long |
| very short, very short to short, short, short to medium, medium, medium to long, long, long to very long, very long | |
| Skin color: | Not mottled |
| not mottled, mottled or speckled with yellow | |
| Yellowish blossomed stripes: | Absent |
| absent, extend less than ⅓ of fruit length, extend more than ⅓ of fruit length | |
| Predominant color at stem end: | Dark green |
| white, light green, medium green, dark green | |
| Predominant color at blossom end: | Medium green |
| white, light green, medium green, dark green | |
| Fruit neck shape: | Necked |
| not necked, necked | |
| Fruit tapering: | End Blunt |
| Both ends tapered, stem end tapered, blossom end tapered, ends blunt or rounded | |
| Skin thickness: | Thin |
| thick; thin | |

TABLE 1-continued

Characteristics of Cucumber Variety NUN 13088 CUL

| Characteristics | Application Variety (NUN 13088 CUL) |
| --- | --- |
| Skin ribs: | Ribbed |
| not ribbed, ribbed | |
| Skin toughness: | Tender |
| tough, tender | |
| Skin luster: | Glossy |
| dull, glossy | |
| Spine color: | White |
| white, black | |
| Spine quality: | Fine |
| coarse, fine | |
| Spine density: | Few |
| few, many | |
| Tubercles (warts): | Few, obscure |
| few, obscure; many, obscure; few, prominent; many, prominent | |
| Type of vestiture: | Prickles only |
| hairs only, hairs and prickles, prickles only | |
| Flavor: bitterfree, bitter | Bitter free |
| Disease resistances: | |
| *Podosphaera xanthii* (Sf) (Powdery mildew) | Highly resistant |
| Cucumber Green Mottle Mosaic Virus (CGMMV) | Highly resistant |

TABLE 2

Objective Description of Cucumber Variety NUN 13088 CUL and the Reference Variety (USDA Descriptors)

| Characteristics | Application Variety (NUN 13088 CUL) | Reference Variety (Verdon) |
| --- | --- | --- |
| Type: | | |
| Predominant usage: | Fresh market | Fresh market |
| Slicing (Fresh Market), Pickling | | |
| Predominant Culture: | Greenhouse, | Greenhouse |
| Outdoor; Greenhouse | low wire | |
| Area of Best Adaptation in the USA: | All areas | All areas |
| North, South, Most Areas | | |
| Maturity: | | |
| Days from seedling to market maturity: | 19 days | NR |
| Plant: | | |
| Habit: | Vine | Vine |
| Bush, Semi-bush, Vine | | |
| Growth: | Indeterminate | Indeterminate |
| Determinate, Indeterminate | | |
| Sex: | Gynoecious | Gynoecious |
| Andromonoecious, Monoecious, Primarily gynoecious | | |
| Flower color: | Yellow | Yellow |
| Yellow, Orange, Green, Other | RHS 6A | RHS 6A |
| Main Stem: | | |
| 3$^{rd}$ internode length, cm: | 117.88 cm | 98.63 cm |
| Stem form: | Grooved, | Grooved, |
| Grooved, ridged; Smooth, round | rigid | rigid |
| Leaf (Mature blade of third leaf): | | |
| Length, cm: | 38.97 cm | 35.25 cm |
| Width, cm: | 36.99 cm | 32.23 cm |
| Petiole length, cm: | 29.59 cm | 23.85 cm |

TABLE 2-continued

Objective Description of Cucumber Variety NUN 13088
CUL and the Reference Variety (USDA Descriptors)

| Characteristics | Application Variety (NUN 13088 CUL) | Reference Variety (Verdon) |
|---|---|---|
| Fruit at edible maturity: | | |
| Length, cm: | 36.31 cm | 35.09 cm |
| Diameter at medial, mm: | 42.09 mm | 42.42 mm |
| Weight, gram: | 440.40 g | 424.0 g |
| Skin color: Not mottled, Mottled or speckled with yellow | Not mottled | Not mottled |
| Yellowish blossom end stripes: Absent, Extend less than ⅓ of the fruit length, Extend more than ⅓ of the fruit length | Absent | Extend less than ⅓ of the fruit length |
| Predominant color at stem end: White, Light Green, Medium Green, Dark Green | Dark green RHS N137A | Dark green RHS N147A |
| Predominant color at blossom end: White, Light Green, Medium Green, Dark Green | Medium green RHS 144A | Medium green RHS 144A |
| Fruit neck shape: Not necked, necked | Necked | Necked |
| Fruit tapering: Both ends tapered, Stem end tapered, Blossom end tapered, Ends blunt or rounded | Ends blunt or rounded | Blossom end tapers |
| Stem end cross section: Circular, Triangular, Square | Circular | Circular |
| Medial cross section: Circular, Triangular, Square | Circular | Circular |
| Blossom end cross section: Circular, Triangular, Square | Triangular | Triangular |
| Skin thickness: Thick, Thin | Thin | Thin |
| Skin ribs: Not ribbed, Ribbed | Ribbed | Ribbed |
| Skin toughness: Tough, Tender | Tender | Tender |
| Skin luster: Dull, Glossy | Glossy | Glossy |
| Spine color: White, Black | White | White |
| Spine quality: Coarse, Fine | Fine | Fine |
| Spine density Few, Many | Few | Few |
| Tubercles (Warts): Few, obscure; Many, obscure; Few, prominent; Many, prominent | Few, obscure | Few, obscure |
| Flavor: Bitter free, Bitter | Bitter free | Bitter free |
| Disease resistances: | | |
| *Cladosporium cucumerinum*(Ccu) | Absent | Highly resistant |
| Cucumber Mosaic Virus (CMV) | Absent | Intermediately resistant |
| *Podosphaera xanthii* (Powdery mildew) | Highly resistant | Highly resistant |
| *Corynespora cassiicola* (Corynespora blight and target leaf spot) | Absent | Highly resistant |
| Cucumber Vein Yellowing Virus (CVYV) | Absent | Intermediately resistant |
| Cucumber Green Mottle Mosaic Virus (CGMMV) | Highly resistant | Highly resistant |

TABLE 3

| Characteristics | Application Variety (NUN 13088 CUL) | Reference Variety (Verdon) |
|---|---|---|
| Objective Description of Cucumber Variety NUN 13088 CUL and the Reference Variety (Non-USDA Descriptors) | | |
| Cotyledon (bitterness):<br>absent, present | Absent | Absent |
| Plant: | | |
| Stem diameter, mm: | 13.09 mm | 12.67 mm |
| Growth type:<br>standard indeterminant, standard<br>determinant, indeterminant,<br>determinant | Indeterminate | Indeterminate |
| Total length of first 15 internodes:<br>very short, very short to short,<br>short, short to medium, medium,<br>medium to long, long to very long,<br>very long | Medium to long | Medium |
| Total length of first 15 internodes,<br>cm: | 137.98 cm | 120.60 cm |
| Number of flowers per node:<br>predominantly one, predominantly<br>one or two, predominantly two,<br>predominantly two or three,<br>predominantly three or four,<br>predominantly four or five,<br>predominantly more than five | Predominantly<br>one | Predominantly<br>one or two |
| Time of development of female<br>flowers:<br>very early, early, medium, late,<br>very late | Very early | Early to<br>medium |
| Parthenocarpy:<br>absent, present | Present | Present |
| Leaf (mature blade): | | |
| Attitude:<br>erect, horizontal, drooping | Horizontal | Horizontal |
| Length:<br>very short, very short to short,<br>short, short to medium, medium,<br>medium to long, long to very long,<br>very long | Long | Medium |
| Ratio length/width of terminal<br>lobe:<br>very small, very small to small,<br>small, small to medium, medium,<br>medium to large, large, large to<br>very large, very large | Medium | Medium |
| Shape of apex of terminal lobe:<br>acute, right-angled, obtuse, rounded | Obtuse | Obtuse |
| Intensity of green color:<br>very light, very light to light,<br>light, light to medium, medium,<br>medium to dark, dark, dark to very<br>dark, very dark | Dark | Dark |
| Blistering:<br>absent or very weak, very weak to<br>weak, weak, weak to medium,<br>medium, medium to strong, strong,<br>strong to very strong, very strong | Weak | Weak |
| Undulation of margin:<br>absent or very weak, moderate,<br>strong | Absent<br>or weak | Absent<br>or weak |
| Dentation of margin:<br>very weak, very weak to weak,<br>weak, weak to medium, medium,<br>medium to strong, strong, strong<br>to very strong, very strong | Weak | Weak |
| Petiole diameter, mm: | 12.14 mm | 10.65 mm |
| Leaf color: | Dark green<br>RHS N137B | Dark green<br>RHS 147A |

TABLE 3-continued

| Characteristics | Objective Description of Cucumber Variety NUN 13088 CUL and the Reference Variety (Non-USDA Descriptors) | |
| --- | --- | --- |
| | Application Variety (NUN 13088 CUL) | Reference Variety (Verdon) |
| Fruit at edible maturity: | | |
| Diameter: | Small to | Small to |
| very small, very small to small, | medium | medium |
| small, small to medium, medium, | | |
| medium to large, large, large to | | |
| very large, very large | | |
| Ratio length/diameter: | Very large | Very large |
| very small, very small to small, | | |
| small, small to medium, medium, | | |
| medium to large, large, large to | | |
| very large, very large | | |
| Core diameter in relation to | Small to | Small to |
| diameter of fruit: | medium | medium |
| very small, very small to small, | | |
| small, small to medium, medium, | | |
| medium to large, large, large to | | |
| very large, very large | | |
| Shape in transverse section: | Round to | Round to |
| round, round to angular, angular | angular | angular |
| Shape of stem end: | Necked | Necked |
| necked, acute, obtuse | | |
| Length of neck: | Long | Long |
| very short, very short to short, | | |
| short, short to medium, medium, | | |
| medium to long, long, long to very | | |
| long, very long | | |
| Shape of calyx end | Obtuse | Obtuse |
| acute, obtuse, rounded, truncate | | |
| Ground color of skin at market | Green | Green |
| stage: | | |
| white, yellow, green | | |
| Intensity of ground color of skin: | Dark | Medium |
| very light, very light to light, | | to dark |
| light, light to medium, medium, | | |
| medium to dark, dark, dark to very | | |
| dark, very dark | | |
| Ribs: | Medium | Medium |
| absent or weak, medium, strong | | |
| Sutures: | Absent | Absent |
| absent, present | | |
| Creasing: | Present | Present |
| absent, present | | |
| Degree of creasing: | Very weak | Weak |
| very weak, very weak to weak, | to weak | |
| weak, weak to medium, medium, | | |
| medium to strong, strong, strong to | | |
| very strong, very strong | | |
| Type of vestiture: | Prickles only | Prickles only |
| hairs only, hairs and prickles, | | |
| prickles only | | |
| Density of vestiture: | Sparse | Sparse to |
| very sparse, very sparse to sparse, | | medium |
| sparse, sparse to medium, medium, | | |
| medium to dense, dense, dense to | | |
| very dense, very dense | | |
| Color of vestiture: | White | White |
| white, light brown, dark brown | | |
| Warts: | Absent | Absent |
| absent, present | | |
| Tubercles/bumps per 2 cm × 2 area: | | |
| Length of stripes: | Absent or | Absent or |
| absent or very short, very short to | very short | very short |
| short, short, short to medium, | | |
| medium, medium to long, long, | | |
| long to very long, very long | | |
| Dots: | Absent | Absent |
| absent, present | | |

TABLE 3-continued

Objective Description of Cucumber Variety NUN 13088
CUL and the Reference Variety (Non-USDA Descriptors)

| Characteristics | Application Variety (NUN 13088 CUL) | Reference Variety (Verdon) |
|---|---|---|
| Glaucosity: absent or very weak, very weak, very weak to weak, weak, weak to medium, medium, medium to strong, strong, strong to very strong, very strong | Absent or very weak | Absent or very weak |
| Peduncle width, mm: | 6.46 mm | 7.05 mm |

TABLE 4

Distinguishing Characteristics between
Cucumber Variety NUN 13088 CUL and the

| Characteristics | Application Variety (NUN 13088 CUL) | Reference Variety (Verdon) |
|---|---|---|
| Plant: | | |
| $3^{rd}$ internode length, cm: | 117.88 cm | 98.63 cm |
| Total length of first 15 internodes: very short, very short to short, short, short to medium, medium, medium to long, long to very long, very long | Medium to long | Medium |
| Total length of first 15 internodes, cm: | 137.98 cm | 120.60 cm |
| Number of flowers per node: predominantly one, predominantly one or two, predominantly two, predominantly two or three, predominantly three or four, predominantly four or five, predominantly more than five | Predominantly one | Predominantly one or two |
| Time of development of female flowers: very early, early, medium, late, very late | Very early | Early to medium |
| Leaf (Mature blade of third leaf): | | |
| Length, cm: | 38.97 cm | 35.25 cm |
| Length: very short, very short to short, short, short to medium, medium, medium to long, long to very long, very long | Long | Medium |
| Width, cm: | 36.99 cm | 32.23 cm |
| Petiole length, cm: | 29.59 cm | 23.85 cm |
| Petiole diameter, mm: | 12.14 mm | 10.65 mm |
| Leaf color: | Dark green RHS N137B | Dark green RHS 147A |
| Fruit at edible maturity: | | |
| Yellowish blossom end stripes: Absent, Extend less than ⅓ of the fruit length, Extend more than ⅓ of the fruit length | Absent | Extend less than ⅓ of the fruit length |
| Predominant color at stem end: White, Light Green, Medium Green, Dark Green | Dark green RHS N137A | Dark green RHS N147A |
| Fruit tapering: Both ends tapered, Stem end tapered, Blossom end tapered, Ends blunt or rounded | Ends blunt or rounded | Blossom end tapers |
| Intensity of ground color of skin: very light, very light to light, light, light to medium, medium, medium to dark, dark, dark to very dark, very dark | Dark | Medium to dark |

TABLE 4-continued

Distinguishing Characteristics between
Cucumber Variety NUN 13088 CUL and the

| Characteristics | Application Variety (NUN 13088 CUL) | Reference Variety (Verdon) |
|---|---|---|
| Degree of creasing: very weak, very weak to weak, weak, weak to medium, medium, medium to strong, strong, strong to very strong, very strong | Very weak to weak | Weak |
| Density of vesture: very sparse, very sparse to sparse, sparse, sparse to medium, medium, medium to dense, dense, dense to very dense, very dense | Sparse | Sparse to medium |
| Disease resistances: | | |
| *Cladosporium cucumerinum*(Ccu) | Absent | Highly resistant |
| Cucumber Mosaic Virus (CMV) | Absent | Intermediately resistant |
| *Corynespora cassiicola* (Corynespora blight and target leaf spot) | Absent | Highly resistant |
| Cucumber Vein Yellowing Virus (CVYV) | Absent | Intermediately resistant |

The results of the T-Test show significant difference at 5% significance level between cucumber variety NUN 13088 CUL and the Reference Variety for $3^{rd}$ internode length, total length of first 15 internodes, mature leaf length, mature leaf width, mature leaf petiole length, and mature leaf petiole width as shown in Tables 5-10.

Table 5 shows a significant difference at 5% significance level between cucumber variety NUN 13088 CUL and the Reference Variety (p<0.001) for $3^{rd}$ internode length (mm) based on a trial conducted in the US in 2023.

TABLE 5

| Statistical Parameter | Application Variety (NUN 13088 CUL) | Reference Variety (VERDON) |
|---|---|---|
| Number of samples | 15 | 15 |
| Minimum | 97.86 | 106.80 |
| Maximum | 131.64 | 138.20 |
| Median | 118.99 | 121.20 |
| Mean | 117.88 | 120.60 |
| Standard deviation | 9.18 | 7.89 |

Table 6 shows a significant difference at 5% significance level between cucumber variety NUN 13088 CUL and the Reference Variety (p<0.001) for total length of first 15 internodes (mm) based on a trial conducted in the US in 2023.

TABLE 6

| Statistical Parameter | Application Variety (NUN 13088 CUL) | Reference Variety (VERDON) |
|---|---|---|
| Number of samples | 15 | 15 |
| Minimum | 118.70 | 106.80 |
| Maximum | 154.40 | 138.20 |
| Median | 140.30 | 121.20 |
| Mean | 137.98 | 120.60 |
| Standard deviation | 9.68 | 7.89 |

Table 7 shows a significant difference at 5% significance level between cucumber variety NUN 13088 CUL and the Reference Variety (p=0.019) for mature leaf length (cm) based on a trial conducted in the US in 2023.

TABLE 7

| Statistical Parameter | Application Variety (NUN 13088 CUL) | Reference Variety (VERDON) |
|---|---|---|
| Number of samples | 15 | 15 |
| Minimum | 33.80 | 25.80 |
| Maximum | 44.20 | 43.30 |
| Median | 39.60 | 34.90 |
| Mean | 38.97 | 35.25 |
| Standard deviation | 3.34 | 4.74 |

Table 8 shows a significant difference at 5% significance level between cucumber variety NUN 13088 CUL and the Reference Variety (p=0.001) for mature leaf width (cm) based on a trial conducted in the US in 2023.

TABLE 8

| Statistical Parameter | Application Variety (NUN 13088 CUL) | Reference Variety (VERDON) |
|---|---|---|
| Number of samples | 15 | 15 |
| Minimum | 32.40 | 26.0 |
| Maximum | 42.0 | 39.20 |
| Median | 37.30 | 31.50 |
| Mean | 36.99 | 32.23 |
| Standard deviation | 2.44 | 4.26 |

Table 9 shows a significant difference at 5% significance level between cucumber variety NUN 13088 CUL and the Reference Variety (p<0.001) for mature leaf petiole length (cm) based on a trial conducted in the US in 2023.

TABLE 9

| Statistical Parameter | Application Variety (NUN 13088 CUL) | Reference Variety (VERDON) |
|---|---|---|
| Number of samples | 15 | 15 |
| Minimum | 24.60 | 19.40 |
| Maximum | 34.40 | 27.90 |
| Median | 29.90 | 24.10 |
| Mean | 29.59 | 23.85 |
| Standard deviation | 2.98 | 2.66 |

Table 10 shows a significant difference at 5% significance level between cucumber variety NUN 13088 CUL and the Reference Variety (p=0.001) for mature leaf petiole diameter (mm) based on a trial conducted in the US in 2023.

TABLE 10

| Statistical Parameter | Application Variety (NUN 13088 CUL) | Reference Variety (VERDON) |
|---|---|---|
| Number of samples | 15 | 15 |
| Minimum | 10.78 | 7.93 |
| Maximum | 13.27 | 12.17 |
| Median | 12.27 | 10.967 |
| Mean | 12.14 | 10.65 |
| Standard deviation | 0.80 | 1.31 |

The results of the T-Test show no significant difference at 5% significance level between cucumber variety NUN 13088 CUL and the Reference Variety for stem diameter, mature fruit weight, mature fruit length, mature fruit diameter at medial, and peduncle width as shown in Tables 11-15.

Table 11 shows no significant difference at 5% significance level between cucumber variety NUN 13088 CUL and the Reference Variety (p=0.224) for stem diameter (mm) based on a trial conducted in the US in 2023.

TABLE 11

| Statistical Parameter | Application Variety (NUN 13088 CUL) | Reference Variety (VERDON) |
|---|---|---|
| Number of samples | 15 | 15 |
| Minimum | 11.43 | 10.84 |
| Maximum | 15.40 | 13.63 |
| Median | 13.19 | 12.69 |
| Mean | 13.09 | 12.67 |
| Standard deviation | 1.10 | 0.74 |

Table 12 shows no significant difference at 5% significance level between cucumber variety NUN 13088 CUL and the Reference Variety (p=0.312) for mature fruit weight (g) based on a trial conducted in the US in 2023.

TABLE 12

| Statistical Parameter | Application Variety (NUN 13088 CUL) | Reference Variety (VERDON) |
|---|---|---|
| Number of samples | 15 | 15 |
| Minimum | 398.0 | 330.0 |
| Maximum | 498.0 | 490.0 |
| Median | 440.0 | 436.0 |
| Mean | 440.40 | 424.0 |
| Standard deviation | 29.16 | 53.99 |

Table 13 shows no significant difference at 5% significance level between cucumber variety NUN 13088 CUL and the Reference Variety (p=0.143) for mature fruit length (cm) based on a trial conducted in the US in 2023.

TABLE 13

| Statistical Parameter | Application Variety (NUN 13088 CUL) | Reference Variety (VERDON) |
|---|---|---|
| Number of samples | 15 | 15 |
| Minimum | 32.20 | 30.60 |
| Maximum | 39.10 | 37.40 |
| Median | 37.20 | 35.90 |
| Mean | 36.31 | 35.09 |
| Standard deviation | 2.27 | 2.19 |

Table 14 shows no significant difference at 5% significance level between cucumber variety NUN 13088 CUL and the Reference Variety (p=0.605) for mature fruit diameter (mm) based on a trial conducted in the US in 2023.

45

TABLE 14

| Statistical Parameter | Application Variety (NUN 13088 CUL) | Reference Variety (VERDON) |
|---|---|---|
| Number of samples | 15 | 15 |
| Minimum | 39.69 | 39.45 |
| Maximum | 44.21 | 45.52 |
| Median | 42.30 | 42.40 |
| Mean | 42.09 | 42.42 |
| Standard deviation | 1.45 | 1.95 |

Table 15 shows no significant difference at 5% significance level between cucumber variety NUN 13088 CUL and the Reference Variety (p=0.067) for peduncle width (mm) based on a trial conducted in the US in 2023.

TABLE 15

| Statistical Parameter | Application Variety (NUN 13088 CUL) | Reference Variety (VERDON) |
|---|---|---|
| Number of samples | 15 | 15 |
| Minimum | 4.86 | 5.67 |
| Maximum | 7.84 | 8.21 |
| Median | 6.54 | 6.99 |
| Mean | 6.46 | 7.05 |
| Standard deviation | 0.91 | 0.78 |

The invention claimed is:

1. A plant or seed of cucumber variety NUN 13088 CUL, wherein a representative sample of seeds of said cucumber variety NUN 13088 CUL has been deposited under Accession Number NCIMB 44043.

2. A plant part of the plant of claim 1, wherein said plant part is a leaf, a fruit, a scion, a root, a rootstock, or a cutting.

3. A seed that produces the plant of claim 1.

4. A cucumber plant, or part thereof, having all of the physiological and morphological characteristics of the plant of claim 1 or part thereof when grown under the same environmental conditions.

5. A tissue culture or cell culture comprising regenerable cells of the plant of claim 1 or part thereof, wherein said cells are obtained from cucumber variety NUN 13088 CUL and are suitable for regeneration into a plant having all of the physiological and morphological characteristics of cucumber variety NUN 13088 CUL.

6. A method of producing the plant of claim 1, said method comprising vegetatively propagating at least a part of the plant of variety NUN 13088 CUL, wherein said part is a cutting, a cell culture, or a tissue culture, and wherein a representative sample of seeds of said cucumber variety has been deposited under Accession Number NCIMB 44043.

7. A vegetatively propagated plant or a part thereof produced by the method of claim 6, wherein the plant or part thereof has all of the physiological and morphological characteristics of variety NUN 13088 CUL when grown under the same environmental conditions, and wherein a representative sample of seeds of said cucumber variety NUN 13088 CUL has been deposited under Accession Number NCIMB 44043.

8. A method of producing a cucumber plant, said method comprising crossing the plant of claim 1 with a second cucumber plant at least once, selecting a progeny cucumber plant from said crossing, and optionally allowing the progeny cucumber plant to form seed.

9. A method of producing a desired trait into the plant of claim 1, said method comprising transforming the plant of claim 1 with a transgene that confers the desired trait, wherein the transformed plant contains the desired trait and otherwise has all of the physiological and morphological characteristics of cucumber variety NUN 13088 CUL, and wherein the desired trait is male sterility, herbicide tolerance, insect resistance, pest resistance, disease resistance, Powdery mildew resistance without necrosis, environmental stress tolerance, modified carbohydrate metabolism, or modified protein metabolism.

10. A method of making doubled haploids of the plant of claim 1, said method comprising making doubled haploid cells from haploid cells of the plant of cucumber variety NUN 13088 CUL, wherein a representative sample of seeds of said cucumber variety NUN 13088 CUL has been deposited under Accession Number NCIMB 44043.

11. A cucumber plant comprising the scion or rootstock of claim 2.

12. A container comprising the plant or seed of claim 1.

13. A food, a feed product, or a processed product comprising the plant part of claim 2, wherein the plant part comprises at least a regenerable cell of cucumber variety NUN 13088 CUL.

14. A method of producing a cucumber fruit, said method comprising growing the plant of claim 1 until it sets at least one fruit, and collecting the fruit.

15. A cucumber fruit produced by the method of claim 14.

16. A method of producing a cucumber plant with a desired trait, comprising mutating a plant or plant part of variety NUN 13088 CUL and selecting a mutated plant with the desired trait, wherein the mutated plant otherwise has all of the physiological and morphological characteristics of cucumber variety NUN 13088 CUL, wherein a representative sample of seeds of said cucumber variety NUN 13088 CUL has been deposited under Accession Number NCIMB 44043, and wherein the desired trait is male sterility, herbicide tolerance, insect resistance, pest resistance, disease resistance, Powdery mildew resistance without necrosis, environmental stress tolerance, modified carbohydrate metabolism, or modified protein metabolism.

17. A method of producing a cucumber seed, said method comprises crossing cucumber plants and harvesting the resultant seed, wherein at least one cucumber plant is the plant of cucumber variety NUN 13088 CUL of claim 1, and wherein a representative sample of seeds of said cucumber variety NUN 13088 CUL has been deposited under NCIMB Accession Number 44043.

18. A method for developing a cucumber plant in a cucumber breeding program, said method comprises applying plant breeding techniques to the plant of claim 1 or part thereof, wherein said plant breeding techniques result in the development of a cucumber plant.

19. A method of producing a cucumber plant derived from the plant of claim 1, comprising:
  a. producing a progeny cucumber plant derived from cucumber variety NUN 13088 CUL by crossing the plant of claim 1 with itself or with a second cucumber plant;
  b. crossing the progeny plant with itself or a different cucumber plant to produce seeds of a progeny plant of a subsequent generation;
  c. growing a progeny plant of the subsequent generation from said seed and crossing the progeny plant of the subsequent generation with itself or another cucumber plant; and
  d. repeating steps (b) and (c) for at least one more generation to produce a cucumber plant further derived from cucumber variety NUN 13088 CUL.

20. A method of producing a modified cucumber plant, said method comprising mutating a target gene by targeted gene editing in a plant or a plant part of cucumber variety NUN 13088 CUL, wherein said target gene modifies a desired trait, wherein the desired trait is male sterility, herbicide tolerance, insect resistance, pest resistance, disease resistance, environmental stress tolerance, modified carbohydrate metabolism, or modified protein metabolism, and wherein a representative sample of seeds of said cucumber variety NUN 13088 CUL has been deposited under Accession Number NCIMB 44043.

21. A modified cucumber plant produced by the method of claim 20, wherein said plant comprises the desired trait and otherwise has all of the physiological and morphological characteristics of cucumber variety NUN 13088 CUL.

\* \* \* \* \*